(12) United States Patent
Penn et al.

(10) Patent No.: US 6,731,976 B2
(45) Date of Patent: May 4, 2004

(54) DEVICE AND METHOD TO MEASURE AND COMMUNICATE BODY PARAMETERS

(75) Inventors: Richard D. Penn, Chicago, IL (US); Keith Alan Miesel, St. Paul, MN (US); Lee Stylos, Stillwater, MN (US); Mark A. Christopherson, Shoreview, MN (US); Sudha Nagavarapu, St. Paul, MN (US); Glenn M. Roline, Anoka, MN (US)

(73) Assignee: Medtronic, Inc., Minneapolis, MN (US)

( * ) Notice: Subject to any disclaimer, the term of this patent is extended or adjusted under 35 U.S.C. 154(b) by 28 days.

(21) Appl. No.: 09/909,485

(22) Filed: Jul. 20, 2001

(65) Prior Publication Data

US 2002/0052563 A1 May 2, 2002

Related U.S. Application Data

(63) Continuation-in-part of application No. 09/299,774, filed on Apr. 26, 1999, now Pat. No. 6,248,080, which is a continuation-in-part of application No. 09/182,971, filed on Oct. 30, 1998, now Pat. No. 6,198,952, and a continuation-in-part of application No. 09/182,972, filed on Oct. 30, 1998, now Pat. No. 6,125,290, and a continuation-in-part of application No. 09/182,863, filed on Oct. 30, 1998, now Pat. No. 6,134,459, and a continuation-in-part of application No. 09/182,970, filed on Oct. 30, 1998, now Pat. No. 6,144,866, and a continuation-in-part of application No. 09/182,764, filed on Oct. 30, 1998, now Pat. No. 6,125,291

(60) Provisional application No. 60/219,676, filed on Jul. 21, 2000.

(51) Int. Cl.[7] .................................................. A61B 5/00
(52) U.S. Cl. ........................ 600/544; 600/549; 600/561
(58) Field of Search .............................. 600/474, 549, 600/561, 544

(56) References Cited

U.S. PATENT DOCUMENTS

| 3,325,799 A | 6/1967 | Farris ....................... 340/573.1 |
| 3,631,438 A | 12/1971 | Lewin ...................... 340/573.1 |
| 3,658,052 A | 4/1972 | Alter .......................... 600/534 |

(List continued on next page.)

FOREIGN PATENT DOCUMENTS

| EP | 0 135 840 A2 | 4/1985 | ............ A61B/5/00 |
| EP | 0 314 937 B1 | 5/1989 | ............ A61B/5/14 |
| EP | 0 279 004 B1 | 7/1989 | ............ A61B/5/00 |
| EP | 0 299 613 B1 | 7/1989 | .......... A61N/1/365 |
| EP | 0 518 364 A2 | 12/1992 | ............ A61N/1/05 |
| WO | WO 80/01620 | 8/1980 | .......... C03C/27/04 |
| WO | WO 94/13200 | 6/1994 | ............ A61B/5/03 |
| WO | WO 96/25978 | 8/1996 | .......... A61N/1/365 |
| WO | WO 98/33451 | * 8/1998 | .......... A61B/19/00 |
| WO | WO 00/30534 | 6/2000 | ............ A61B/5/00 |

OTHER PUBLICATIONS

W.H. Ko et al., "A Design of Capacitive Pressure Transducer," IEEE: New York 1984.

V. Gaeger, R. Kobs and M. Liehr, "A Ceramic Differential-–Pressure Transducer," Philips Tech., Rev. 43, S6–93.

(List continued on next page.)

*Primary Examiner*—Carl Layno
(74) *Attorney, Agent, or Firm*—Shumaker & Sieffert, P.A.

(57) ABSTRACT

A system and method for measuring and communicating parameters of a brain, tissue, or other organs is disclosed. The system includes a sensor to sense the parameter of interest, an external device where the parameter may be displayed, processed or cause action to be taken, and a communication system to communicate the sensed parameter from the sensor to the external device. In another embodiment, the system includes a processing system for processing the sensed parameters and controlling an associated medical device.

81 Claims, 20 Drawing Sheets

U.S. PATENT DOCUMENTS

| | | | |
|---|---|---|---|
| 3,669,094 A | 6/1972 | Heyer | 600/561 |
| 3,746,087 A | 7/1973 | Lavering et al. | 165/185 |
| 3,757,770 A | 9/1973 | Brayshaw et al. | 600/302 |
| 3,782,368 A | 1/1974 | Reibold | 600/500 |
| 3,796,208 A | 3/1974 | Bloice | 600/534 |
| 3,802,419 A | 4/1974 | Yates | 600/536 |
| 3,847,483 A | 11/1974 | Shaw et al. | 356/41 |
| 3,875,929 A | 4/1975 | Grant | 600/429 |
| 3,911,899 A | 10/1975 | Hattes | 600/561 |
| 3,943,915 A | 3/1976 | Severson | 600/407 |
| 4,026,276 A * | 5/1977 | Chubbuck | 600/407 |
| 4,036,217 A | 7/1977 | Ito et al. | 600/536 |
| 4,062,354 A | 12/1977 | Taylor et al. | 600/302 |
| 4,066,072 A | 1/1978 | Cummins | 601/15 |
| 4,080,653 A | 3/1978 | Barnes, Jr. et al. | 600/561 |
| 4,114,603 A | 9/1978 | Wilkinson | 600/561 |
| 4,114,604 A | 9/1978 | Shaw et al. | 600/339 |
| 4,114,606 A | 9/1978 | Seylar | 600/409 |
| 4,146,885 A | 3/1979 | Lawson, Jr. | 600/534 |
| 4,147,161 A | 4/1979 | Ikebe et al. | 600/561 |
| 4,169,462 A | 10/1979 | Strube | 600/534 |
| 4,185,621 A | 1/1980 | Morrow | 600/485 |
| 4,186,749 A | 2/1980 | Fryer | 600/561 |
| 4,202,339 A | 5/1980 | Wirtzfeld et al. | 607/22 |
| 4,246,908 A | 1/1981 | Inagaki et al. | 600/561 |
| 4,269,195 A | 5/1981 | Itoh | 600/536 |
| 4,281,651 A | 8/1981 | Cox | 128/204.23 |
| 4,281,666 A | 8/1981 | Cosman | 600/561 |
| 4,281,667 A | 8/1981 | Cosman | 600/561 |
| 4,354,506 A | 10/1982 | Sakaguchi et al. | 600/561 |
| 4,361,153 A | 11/1982 | Slocum et al. | 607/32 |
| 4,378,809 A | 4/1983 | Cosman | 600/561 |
| 4,385,636 A | 5/1983 | Cosman | 600/561 |
| 4,393,878 A | 7/1983 | Kahn | 600/561 |
| 4,399,820 A | 8/1983 | Wirtzfeld et al. | 607/21 |
| 4,407,296 A | 10/1983 | Anderson | 600/488 |
| 4,421,386 A | 12/1983 | Podgorski | 359/871 |
| 4,443,730 A | 4/1984 | Kitamura et al. | 310/330 |
| 4,444,498 A | 4/1984 | Heinemann | 356/246 |
| 4,467,807 A | 8/1984 | Bornzin | 607/22 |
| 4,471,786 A | 9/1984 | Inagaki et al. | 600/561 |
| 4,485,813 A | 12/1984 | Anderson et al. | 600/488 |
| 4,494,545 A | 1/1985 | Slocum et al. | 607/32 |
| 4,519,401 A * | 5/1985 | Ko et al. | 600/561 |
| 4,523,279 A | 6/1985 | Sperinde et al. | 600/323 |
| 4,540,002 A | 9/1985 | Atlas | 600/547 |
| 4,554,927 A | 11/1985 | Fussell | 600/483 |
| 4,564,022 A | 1/1986 | Rosenfeld et al. | 600/561 |
| 4,600,013 A | 7/1986 | Landy et al. | 600/561 |
| 4,621,647 A | 11/1986 | Loveland | 600/561 |
| 4,623,248 A | 11/1986 | Sperinde | 356/41 |
| 4,630,614 A | 12/1986 | Atlas | 600/534 |
| 4,651,741 A | 3/1987 | Passafaro | 600/328 |
| 4,653,508 A | 3/1987 | Cosman | 600/561 |
| 4,660,568 A | 4/1987 | Cosman | 600/561 |
| 4,676,255 A | 6/1987 | Cosman | 600/561 |
| 4,677,985 A | 7/1987 | Bro et al. | 600/504 |
| 4,697,593 A | 10/1987 | Evans et al. | 600/343 |
| 4,703,756 A | 11/1987 | Gough et al. | 600/347 |
| 4,705,499 A | 11/1987 | Hooven | 604/9 |
| 4,727,879 A | 3/1988 | Liess et al. | 600/333 |
| 4,730,389 A | 3/1988 | Baudino et al. | 29/825 |
| 4,730,622 A | 3/1988 | Cohen | 600/480 |
| 4,738,267 A | 4/1988 | Lazorthes et al. | 600/561 |
| 4,739,771 A * | 4/1988 | Manwaring | 600/504 |
| 4,744,029 A | 5/1988 | Raviv et al. | 600/544 |
| 4,750,495 A | 6/1988 | Moore et al. | 607/22 |
| 4,753,246 A | 6/1988 | Freeman | 600/544 |
| 4,791,935 A | 12/1988 | Baudino et al. | 600/333 |
| 4,796,641 A | 1/1989 | Mills et al. | 600/561 |
| 4,807,629 A | 2/1989 | Baudino et al. | 607/22 |
| 4,807,632 A | 2/1989 | Liess et al. | 600/333 |
| 4,813,421 A | 3/1989 | Baudino et al. | 600/333 |
| 4,815,469 A | 3/1989 | Cohen et al. | 600/333 |
| 4,827,933 A | 5/1989 | Koning et al. | 607/22 |
| 4,830,488 A | 5/1989 | Heinze et al. | 600/325 |
| 4,841,986 A | 6/1989 | Marchbanks | 600/559 |
| 4,846,191 A | 7/1989 | Brockway et al. | 600/561 |
| 4,858,619 A | 8/1989 | Toth | 600/561 |
| 4,877,032 A | 10/1989 | Heinze et al. | 607/2 |
| 4,885,002 A * | 12/1989 | Watanabe et al. | 604/9 |
| 4,893,630 A | 1/1990 | Bray, Jr. | 600/484 |
| 4,893,703 A | 1/1990 | Kennedy et al. | 192/58.61 |
| 4,903,701 A | 2/1990 | Moore et al. | 607/22 |
| 4,903,707 A | 2/1990 | Knute et al. | 600/561 |
| 4,967,755 A | 11/1990 | Pohndorf | 600/488 |
| 4,971,061 A | 11/1990 | Kageyama et al. | 600/438 |
| 4,974,602 A | 12/1990 | Abraham-Fuchs et al. | 650/544 |
| 4,984,567 A | 1/1991 | Kageyama et al. | 600/438 |
| 4,987,897 A | 1/1991 | Funke | 600/561 |
| 4,995,401 A | 2/1991 | Bunegin et al. | 600/561 |
| 5,005,573 A | 4/1991 | Buchanan | 128/207.14 |
| 5,031,618 A | 7/1991 | Mullett | 607/46 |
| 5,040,533 A | 8/1991 | Fearnot | 607/22 |
| 5,040,538 A | 8/1991 | Mortazavi | 600/333 |
| 5,052,388 A | 10/1991 | Sivula et al. | 607/22 |
| 5,054,497 A | 10/1991 | Kapp et al. | 600/561 |
| 5,058,586 A | 10/1991 | Heinze | 600/341 |
| 5,074,310 A | 12/1991 | Mick | 600/561 |
| 5,113,859 A | 5/1992 | Funke | 607/4 |
| 5,113,862 A | 5/1992 | Mortzavi | 600/331 |
| 5,113,868 A | 5/1992 | Wise et al. | 600/488 |
| 5,113,869 A | 5/1992 | Nappholz et al. | 600/508 |
| 5,117,835 A | 6/1992 | Mick | 600/561 |
| 5,117,836 A | 6/1992 | Millar | 600/561 |
| H1114 H | 12/1992 | Schweitzer et al. | 600/325 |
| 5,176,138 A | 1/1993 | Thacker | 607/22 |
| 5,191,898 A | 3/1993 | Millar | 600/561 |
| 5,195,529 A | 3/1993 | Malkamaki | 600/529 |
| 5,199,428 A | 4/1993 | Obel et al. | 607/44 |
| 5,215,086 A | 6/1993 | Terry, Jr. et al. | 607/46 |
| 5,234,567 A | 8/1993 | Hobbs et al. | 204/415 |
| 5,267,564 A | 12/1993 | Barcel et al. | 600/310 |
| 5,275,171 A | 1/1994 | Barcel | 607/122 |
| 5,291,899 A | 3/1994 | Watanabe et al. | 600/561 |
| 5,312,454 A | 5/1994 | Roline et al. | 607/22 |
| 5,324,326 A | 6/1994 | Lubin | 607/122 |
| 5,325,865 A | 7/1994 | Beckman et al. | 600/561 |
| 5,329,922 A | 7/1994 | Atlee, III | 600/328 |
| 5,342,406 A | 8/1994 | Thompson | 607/22 |
| 5,358,519 A | 10/1994 | Grandjean | 623/312 |
| 5,377,524 A | 1/1995 | Wise et al. | 73/1.34 |
| 5,411,024 A | 5/1995 | Thomas et al. | 600/325 |
| 5,411,532 A | 5/1995 | Mortazavi | 607/22 |
| 5,438,987 A | 8/1995 | Thacker et al. | 600/337 |
| 5,490,323 A | 2/1996 | Thacker et al. | 29/825 |
| 5,517,998 A | 5/1996 | Madison | 600/473 |
| 5,535,752 A | 7/1996 | Halperin et al. | 600/483 |
| 5,549,654 A | 8/1996 | Powell | 607/32 |
| 5,556,421 A | 9/1996 | Prutchi et al. | 607/36 |
| 5,564,434 A | 10/1996 | Halperin et al. | 600/488 |
| 5,593,430 A | 1/1997 | Renger | 607/18 |
| 5,593,431 A | 1/1997 | Sheldon | 607/19 |
| 5,596,995 A | 1/1997 | Sherman et al. | 600/549 |
| 5,601,611 A | 2/1997 | Fayram et al. | 607/6 |
| 5,617,873 A | 4/1997 | Yost et al. | 600/561 |
| 5,637,083 A | 6/1997 | Bertrand et al. | 604/9 |
| 5,683,422 A | 11/1997 | Rise | 607/2 |
| 5,683,432 A | 11/1997 | Goedeke et al. | 607/32 |
| 5,704,352 A * | 1/1998 | Tremblay et al. | 600/300 |
| 5,710,735 A | 1/1998 | Shin et al. | 365/185.26 |

| | | | |
|---|---|---|---|
| 5,730,125 A | 3/1998 | Prutchi et al. | 600/323 |
| 5,743,267 A | 4/1998 | Nikolic et al. | 600/483 |
| 5,752,976 A | 5/1998 | Duffin et al. | 607/32 |
| 5,758,652 A | 6/1998 | Nikolic | 600/487 |
| 5,788,647 A | 8/1998 | Eggers | 600/526 |
| 5,792,186 A | 8/1998 | Rise | 607/2 |
| 5,795,307 A * | 8/1998 | Krueger | 600/561 |
| 5,817,137 A | 10/1998 | Kaemmerer | 607/59 |
| 5,833,603 A | 11/1998 | Kovacs et al. | 600/317 |
| 5,843,139 A | 12/1998 | Goedeke et al. | 607/32 |
| 5,873,840 A | 2/1999 | Neff | 600/561 |
| 5,904,708 A | 5/1999 | Goedeke | 607/18 |
| 5,919,221 A | 7/1999 | Miesel | 607/119 |
| 6,015,386 A | 1/2000 | Kensey et al. | 600/486 |
| 6,045,530 A | 4/2000 | Krueger et al. | 604/95.04 |
| 6,064,910 A | 5/2000 | Andersson et al. | 607/20 |
| 6,113,553 A | 9/2000 | Chubbuck | 600/561 |
| 6,165,135 A | 12/2000 | Neff | 600/561 |
| 6,201,980 B1 | 3/2001 | Darrow et al. | 600/347 |
| 6,248,080 B1 | 6/2001 | Miesel et al. | 600/561 |
| 6,267,724 B1 | 7/2001 | Taylor | 600/309 |
| 6,315,721 B2 | 11/2001 | Schulman et al. | 600/301 |
| 6,360,122 B1 | 3/2002 | Fischell et al. | 600/544 |
| 6,387,051 B1 | 5/2002 | Ragauskas et al. | 600/438 |

OTHER PUBLICATIONS

J.F. Dias et al., "Capacitive Blood Pressure Transducer," ISA Transactions, vol. 19, No. 3, pp. 19–23, 1980.

Hin–Leung Chau, Member, IEEE, and Kensall D. Wise, Fellow, IEEE, "An Ultraminiature Solid–State Pressure Sensor for a Cardiovascular Catheter," IEEE Trans. Electron Devices, vol. 35, No. 12, pp. 2355–2362, Dec. 1988.

"Capacitive Transducers," Capacitive Gaging System, courtesy of Lion Precision Corp., Newton, Mass. Section 4.1, in part, is from Harry E. Thomas Handbook of Biomedical Instrumentation and Measurement, Reston Publishing Co., reston, VA., 1974, p. 12.

R. V. Jones and J C S Richards, "The Design and Some Applications of Sensitive Capacitance Micrometers," Natural Philosophy Department, Aberdeen University, Aberdeen AB9 2UE, pp. 589–600, 1973.

* cited by examiner

SECTION A-A

SECTION A-A

DEVICE AND METHOD TO MEASURE AND COMMUNICATE BODY PARAMETERS

This application claims the benefit of U.S. Provisional Application No. 60/219,676, filed Jul. 21, 2000 and is a continuation-in-part of application Ser. No. 09/299,774, filed Apr. 26, 1999, now Pat. No. 6,248,080, which is a continuation-in-part of application Ser. No. 09/182,971, filed on Oct. 30, 1998, now Pat. No. 6,198,952, application Ser. No. 09/182,972, filed on Oct. 30, 1998, now Pat. No. 6,125,290, application Ser. No. 09/182,863, filed on Oct. 30, 1998, now Pat No. 6,134,459, application Ser. No. 09/182,970, filed on Oct. 30, 1998, now Pat. No. 6,144,866, application Ser. No. 09/182,764, filed on Oct. 30, 1998 now Pat. No. 6,125,291, and application Ser. No. 08/923,079, filed on Sep. 3, 1997, now Pat. No. 5,902,326.

FIELD OF THE INVENTION

The present invention relates to a device and method for measuring and communicating parameters of a brain, tissue or other organs, especially the intracranial pressure or temperature or both in a brain.

BRIEF DESCRIPTION OF RELATED ART

A typical adult has a total of about 120–150 cc of (cerebrospinal fluid) CSF with about 25 cc in the ventricles in the brain. A typical adult also produces about 500 cc/day of CSF, all of which is reabsorbed into the blood stream on a continuous basis.

Different conditions can cause the CSF pressure to vary, often in an increasing and dangerous manner. For example, hydrocephalus is a condition of excessive accumulation of CSF in the ventricles or brain cavities. Hydrocephalus can result from congenital conditions interfering with normal CSF circulation or as the result of a problem with CSF re-absorption.

Excessive accumulation of CSF due to hydrocephalus causes increased pressure upon the brain. Whatever the cause, over time, this increased CSF pressure causes damage to the brain tissue. It has been found that shunting the excess CSF to another area of the body is therapeutically beneficial and generally allows the patient to lead a full and active life.

To treat the condition of hydrocephalus, a shunt is used as a conduit to transport CSF from one location in the body to another, for example to the peritoneal cavity or atrium of the heart. A typical shunt for transporting CSF from the ventricle to another part of the body is comprised of a ventricular catheter, valve and distal catheter. CSF shunts also exist for transporting fluid from the spine to another part of the body such as the peritoneal cavity.

Examples of systems to continuously drain excess CSF from the ventricles of the brain are the Delta® Shunt and the CSF—Flow Control Shunt Assembly made and sold by Medtronic—PS Medical of Goleta, California and as disclosed in U.S. Pat. No. 4,560,375 entitled "Flow Control Valve", issued Dec. 24, 1985 to Rudolf R. Schulte, Gary P. East, Marga M. Bryant and Alfons Heindl. Such systems use a drainage catheter 2 that is placed in the patient's ventricle 4 in the brain (FIG. 1). The drainage catheter 2 is connected to a valve 6. A ventricular or atrial catheter 8 is connected to the valve 6. The peritoneal or atrial catheter 8 is placed in the patient's peritoneum or atrium of the heart, respectively, to drain the excess CSF. All of these systems continuously transport excess CSF from the patient's ventricle through the drainage catheter 2 to another part of the body. For patients with head trauma, who often have increased intracranial pressure at least over some time period. it is often desirable to continuously drain CSF, usually to an external device, to maintain normal CSF pressure in the brain.

Examples of systems to continuously drain excess CSF to an external device are the Becker System® and the EDM Drainage System® made and sold by Medtronic—PS Medical of Goleta, Calif. Another example of a system to continuously drain excess CSF is shown in U.S. Pat. No. 4,731,056 issued to William S. Tremulis on Mar. 15, 1988 and entitled "External Drainage Antisiphon Device." A further such system is disclosed in U.S. Pat. No. 5,772,625 issued to John A. Krueger, Kevin M. Jaeger and Helmut W. C. Rosenberg on Jun. 30, 1998 and entitled "External Drainage Shunt."

SUMMARY OF THE INVENTION

A device for measuring and communicating parameters of a brain, tissue or other organs is disclosed. The invention includes a sensor to sense the parameter of interest and then communicate the sensed parameter to an external device where the parameter may be displayed, processed or cause action to be taken. The present invention allows chronic and stable measurement and communication of physiologic parameters to be made.

In a preferred embodiment, the device measures and communicates parameters of a brain, tissue or other organs. Particularly, a device for measuring and communicating the intracranial pressure, CSF pressure or temperature in a brain, tissue or other organ is disclosed.

The invention includes a sensor to sense pressure, intracranial pressure, CSF pressure or temperature. The sensor is preferably located at the distal end of a probe and is preferably placed in the area of the brain, tissue or other organ where a measurement is desired such as the parenchyma or ventricles of the brain.

In the preferred embodiment, the sensor is part of a passive system that allows pressure or temperature measurements to be made and communicated to an attending practitioner when the passive system receives power from an external source. The part of the passive system that receives power from the external source and communicates pressure measurements is preferably located on or next to the skull of the patient while the sensor is locate near or at the area where a measurement is desired to be made.

The passive system couples to an external device that provides power to the passive system. This power is used to power the sensing operation of the sensor and to upload the sensed information from the passive system to an external device. As a result, when coupled to the external power source, the passive system is able to measure and uplink measured physiological parameters such as pressure and temperature measurements from the sensor to an external device.

In an alternate embodiment, the sensor is part of a system having a long-term energy source and storage system that allows pressure or temperature measurements to be taken periodically or upon demand, stored and then communicated to an attending practitioner as desired. The part of the system that provides power, stores pressure or temperature measurements and communicates the pressure or temperature measurements is preferably located on or next to the subclavicular region of the patient.

The long-term energy source may be rechargeable. This power from the long-term energy source is used to power the sensing operation of the sensor, store the pressure or temperature measurements and to upload the sensed pressure or temperature information from the system to an external device.

In an alternate embodiment of the invention, the sensed parameter is used to control a pump or valve in a CSF shunt or drainage system. In this embodiment, a pump or valve is placed between a catheter that is placed in the ventricles of the brain and a shunt used as a conduit to transport CSF from one location in the body to another. The pump operates to pump CSF fluid or the valve opens to allow CSF fluid to drain in response to sensed CSF pressure.

The invention also includes, in one embodiment, a method for measuring and communicating parameters of a brain, tissue or other organs. The method includes the steps of providing a sensor to sense the parameter of interest, implanting the sensor in or near a target in the brain, tissue or other organ where the parameter of interest may be sensed, providing a reaction device where the parameter may be displayed, processed or cause action to be taken, sensing the parameter or interest, communicating the sensed parameter to the reaction device and displaying or processing the parameter or causing action to be taken in response to the parameter. In one embodiment of the method, the parameter of interest is the intracranial pressure, CSF pressure or temperature in a brain, tissue or other organ. Also, in another embodiment of the method, the step of providing a sensor includes providing a sensor such as is described herein. Further, in another embodiment of the invention, the method includes the step of providing a CSF shunt or drainage system having a pump or valve and the step of causing action to be taken in response to the parameter includes the step of controlling the pump or valve.

It is an object of one embodiment of the invention to provide a system and method for measuring a physiological parameter such as pressure, intracranial pressure, CSF pressure or temperature that does not require a continuous source of power such as a battery or power capacitor.

It is another object of one embodiment of the invention to provide a device and method that communicates a sensed physiological parameter such as pressure or temperature measurements to an external device.

In another embodiment of the invention, it is an object of the invention to provide a system and method that stores sensed physiological parameters such as sensed pressure or temperature measurements to be uploaded to an external device at a later time.

In a further alternate embodiment of the invention, it is an object of the invention to provide a system and method that actively responds to a sensed physiological parameter to take an action. Specifically, in an alternate embodiment of the invention, it is an object of the invention to provide a CSF shunt or drainage system and method that actively provides information to regulate such shunt or drainage system in response to CSF pressure measurements.

In another alternate embodiment of the invention, it is an object of the invention to provide a sensor of physiological parameters, particularly brain parameters, that requires the tissue of interest to be opened only once to implant the sensor and is thereafter closed and allowed to heal while the implanted sensor provides long-term monitoring of the parameter of interest.

It is an object of the invention in another embodiment of the invention to provide an implantable device that provides information about a body parameter of interest which does not depend on a battery to operate and therefore does not depend on the battery life to remain in operation.

These and other objects of the invention will be clear from the description of the invention contained herein and more particularly with reference to the Figures. Throughout the description, like elements are referred to by like reference numbers. Further, it is clear that to changes to the description contained herein may occur to those skilled in the art and still fall within the scope of the invention. Further, it is clear that the methods of the invention may be practiced with the system or devices shown or may be practiced with other systems and devices as will be clear to those skilled in the art. Therefore, it is not intended that the practice of the methods be limited to such practice only with the specific systems and devices shown.

DETAILED DESCRIPTION OF THE INVENTION

Figure 1:
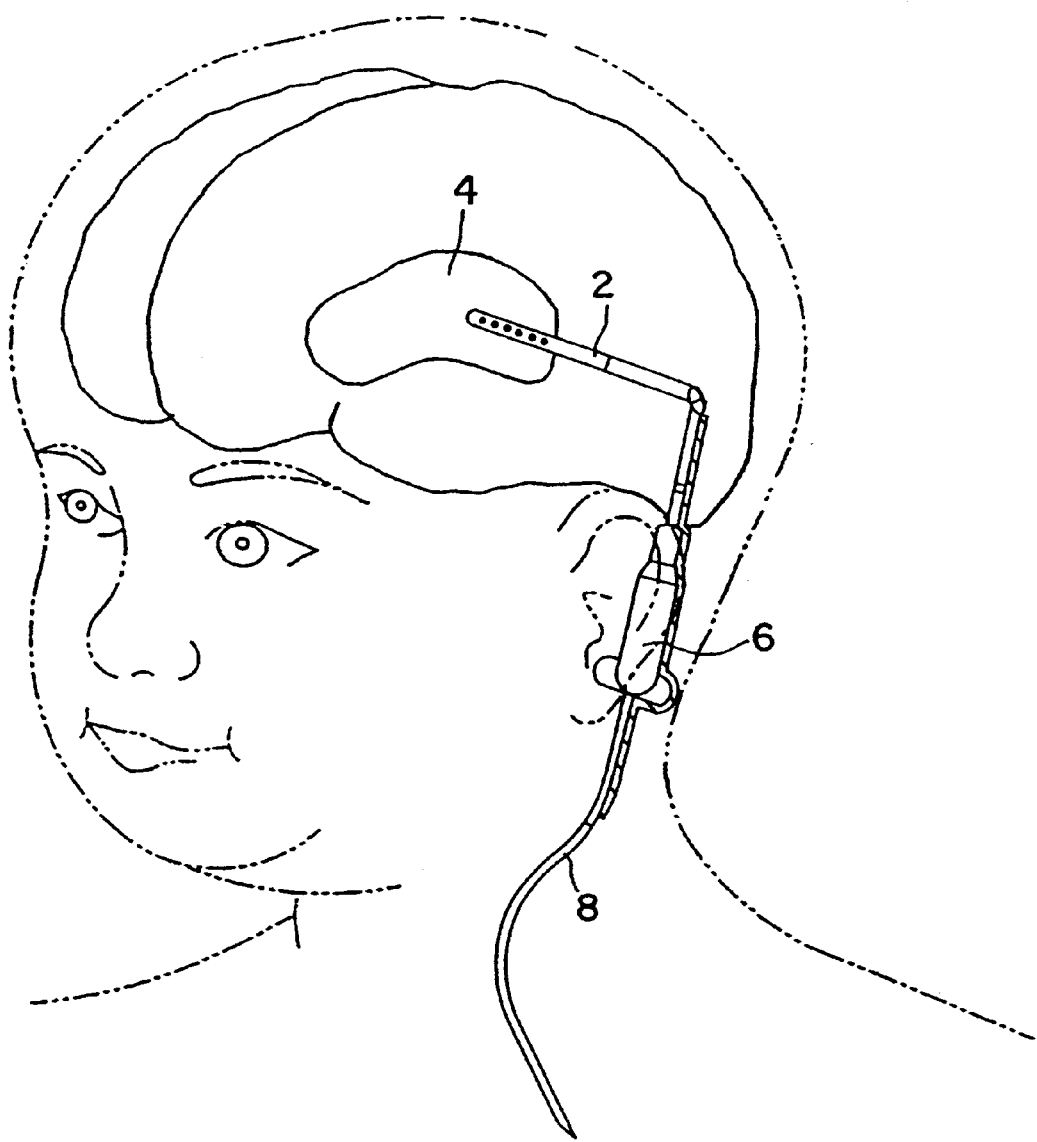
FIG. 1 is a schematic diagram of a CSF shunt drainage system.
Figure 2:
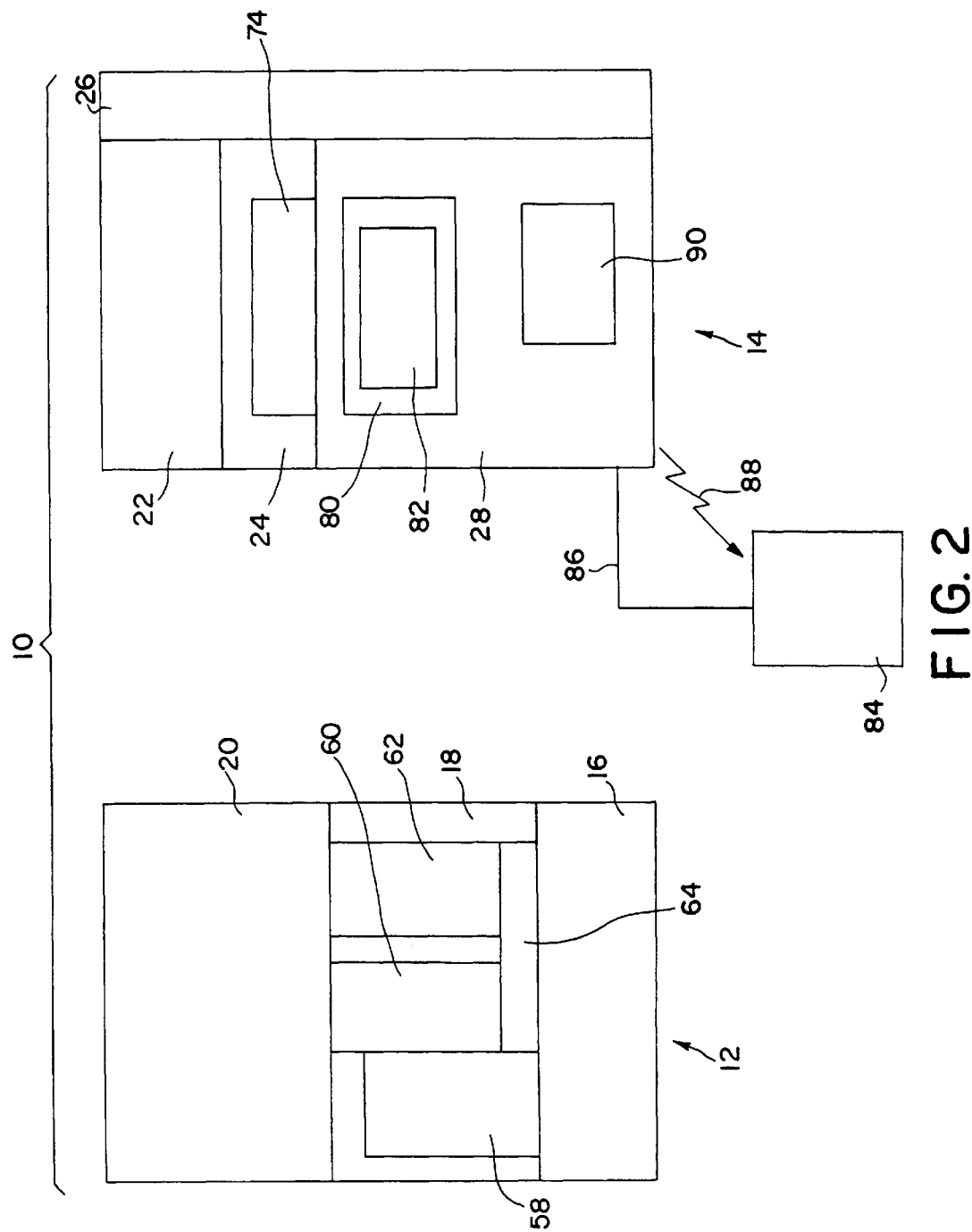
FIG. 2 is a block diagram of the invention.

The device embodying the present invention is shown in FIG. 2 generally labeled 10. The device 10 includes an implanted probe 12 and an external device 14. Probe 12 includes a sensor 16, probe electronics 18 and a probe coil 20. External device 14 includes external coil 22, external electronics 24, a power source 26 and a user communication system 28.

Figure 4:
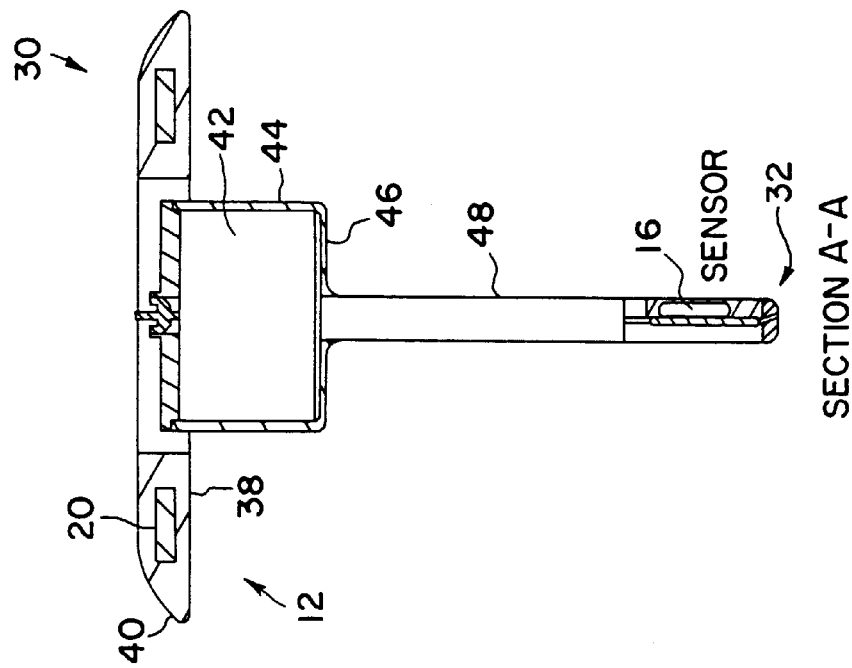
FIG. 4 is a side cross-sectional view of the embodiment of FIG. 3.
Figure 3:
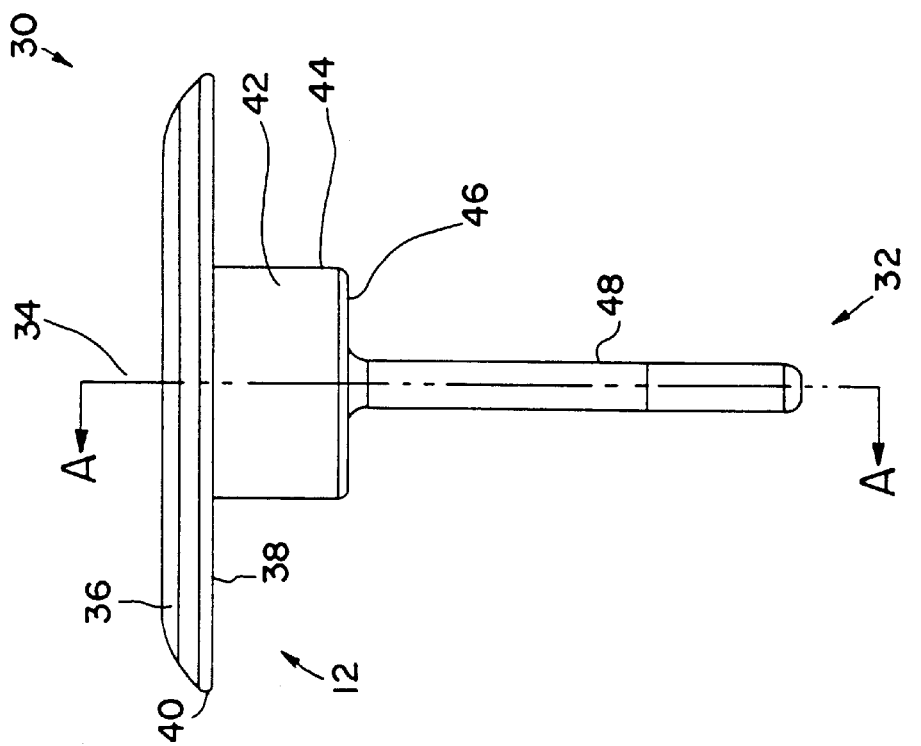
FIG. 3 is a side view of the preferred embodiment of the invention.

In the preferred embodiment of the invention shown in FIGS. 3 and 4, probe 12 has a proximal end 30 and a distal end 32 and a central axis 34. Sensor 16 is preferably located at the distal end 32. Sensor 16 is a sensor capable of sensing pressure such as intracranial pressure. An example of such a sensor is found in co-pending application Ser. No. 09/299,774 by Keith A. Miesel and Lee Stylos entitled "Intracranial Monitoring and Therapy Delivery Control Device, System and Method", assigned to the common assignee of the present invention.

A probe head 36 is located at the proximal end 30. In the preferred embodiment, probe head 36 is roughly discoid in shape and includes an embedded probe coil 20. Probe coil 20 is an inductive coil. In one embodiment shown in FIGS. 3 and 4, probe coil 20 is wound around axis 34 in the plane of probe head 36. Probe head 36 includes an underside 38 and an outer edge 40.

In the embodiment of FIGS. 3 and 4, the probe electronics 18 are stored in an electronics case 42, attached to the underside 38 of probe head 36. The electronics case 42 has a periphery 44 and an underside 46. Electronics case 42 is preferably cylindrical with a smaller diameter around axis 34 than has probe head 36.

As shown in FIGS. 3 and 4, sensor 16 is separated from electronics case 42. This is preferably accomplished by locating sensor 16 at the distal end of a body 48 connected to the underside 46 of electronics case 42. Body 48 may be made of a stiff material such as titanium or a rigid body-compatible plastic like polyurethane. Alternately, body 48 may be made of a flexible material such as a flexible body-compatible plastic such as polyurethane that is inherently flexible by its composition or designed to be flexible by its structural design. In either the rigid or flexible case, the material of body 48 may be any metal, plastic, ceramic or other material that is body-compatible and is as flexible or rigid, in varying degrees, as desired as is well understood in the art.

In the embodiment where body 48 is rigid, sensor 16 will be located at a fixed location relative to the electronics case 42. Where body 48 is flexible, such as in the embodiment shown in FIG. 9, sensor 16 may be placed where desired in the brain, tissue other organs wherever in the body. In particular, where body 48 is flexible, sensor 16 may be placed where the distance from sensor 16 to the electronics case 42 varies as, for example, with movement.

In addition, where body 48 is flexible, sensor 16 may be placed on or in areas where it would be difficult to place sensor 16 where body 48 to be rigid. For example, where body 48 is flexible, sensor 16 may be "slid" between the dura and the skull to a desired position between the dura and the skull.

In a further alternate embodiment, sensor 16 may be connected to electronics case 42 through a system known as a "body bus". The "body bus" is a telemetry system where the patient's own body provides the interconnection between the sensor 16 and the electronics case 42. An example of such a "body-bus" communication system is given in U.S. Pat. Nos. 4,987,897 and 5,113,859, issued to Hermann D. Funke on Jan. 29, 1991 and May 19, 1992, entitled "Body Bus Medical Device Communication System" and "Acoustic Body Bus Medical Device Communication System" respectively, the teachings of which are incorporated herein by reference in its entirety. Alternately, a radio frequency telemetry approach as described in U.S. Pat. No. 5,683,432 to Goedeke may be used to link sensor 16 to electronics case 42.

The sensor 16 is preferably calibrated at the manufacturing site by comparing its measurements with measurements from a standardized sensor. Calibration coefficients, which are unique to each sensor 16, are computed and stored in the external device 14, sensor 16, probe electronics 18, storage device 78 or microprocessor 102 for the purpose of post-measurement processing to achieve an accurate report of the physiological parameters measured by sensor 16.

Because probe 12 will be inserted into the body, probe 12 should be hermetically sealed to prevent the intrusion of body fluids into probe 12.

Figure 5:
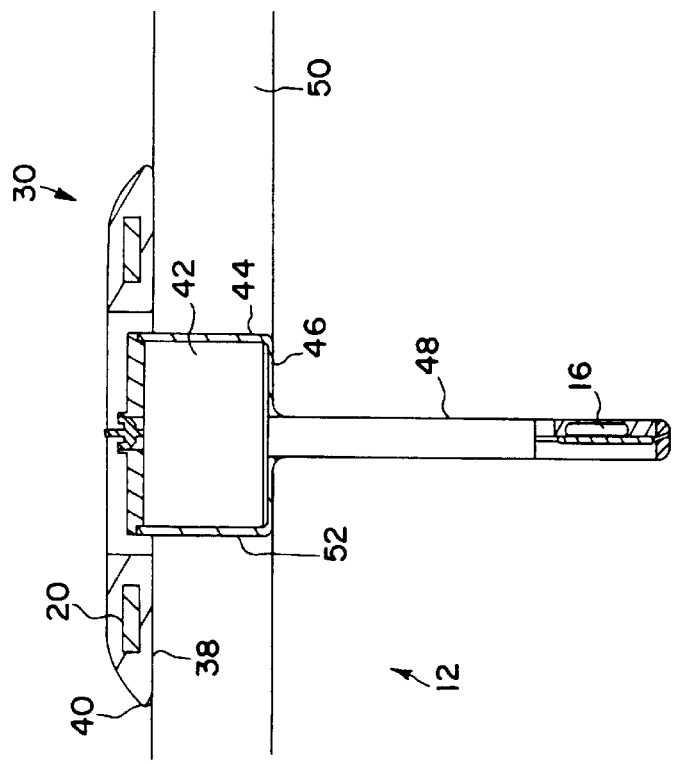
FIG. 5 is a side cross-sectional view of the embodiment of FIG. 3 in place in a skull.

In the preferred embodiment shown in FIGS. 3 and 4, the proximal end 30 is located either immediately outside of or incorporated into the skull 50 of the patient. This is preferably accomplished by making the probe head 36 with a larger diameter around axis 34 than the electronics case 42 has. Then, to place the probe 12, a hole 52 is drilled in skull 50 having a diameter about the same as the diameter of electronics case 42 (FIG. 5). Hole 52 should go entirely through the skull 50 and have the same diameter as the diameter of electronics case 42. The sensor 16 and body 48 of probe 12 is placed through the hole 52 until the electronics case 42 contacts hole 52. Electronics case 42 is then aligned with hole 52 and pushed through hole 52 until the underside 38 of probe head 36 contacts the skull 50. Electronics case 42 should be dimensioned so as not to extend entirely through hole 52.

Alternately, screw threads may be placed around the periphery 44 of electronics case 42. In this embodiment, hole 52 is a threaded hole with threads matching the threads of electronics case 42. Electronics case 42 is brought into contact with hole 52 as described above. However, instead of pushing electronics case 42 through hole 52, electronics case 42 is threaded into hole 52.

Figure 6:
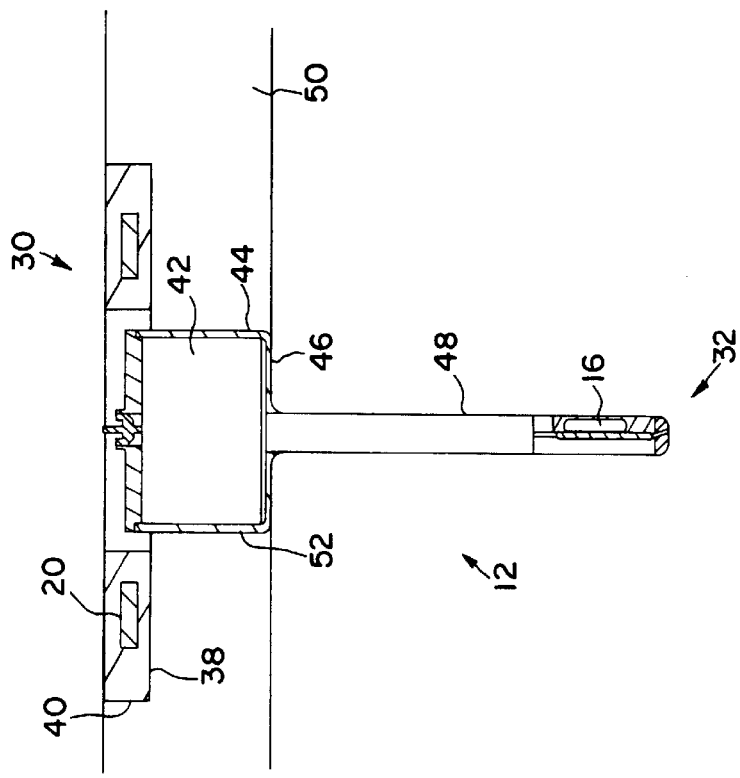
FIG. 6 is a side cross-sectional view of an alternate embodiment of the invention in place in a skull.

In a further alternate embodiment shown in FIG. 6, screw threads are placed on the outer edge 40 of probe head 36. Hole 52 is dimensioned to have a diameter approximately the same as the diameter of probe head 36. In this embodiment as well, hole 52 has threads corresponding to the threads on probe head 36. To place the probe 12, the sensor 16, body 48 and electronics case 42 of probe 12 is placed through the hole 52 until the outer edge 40 of probe head 36 contacts hole 52. Probe head 36 is then aligned with hole 52 and threaded through hole 52 until probe head 36 has a desired orientation, such as flush with the skull 50. In this embodiment, electronics case 42 may or may not have the same diameter as probe head 36.

Figure 7:
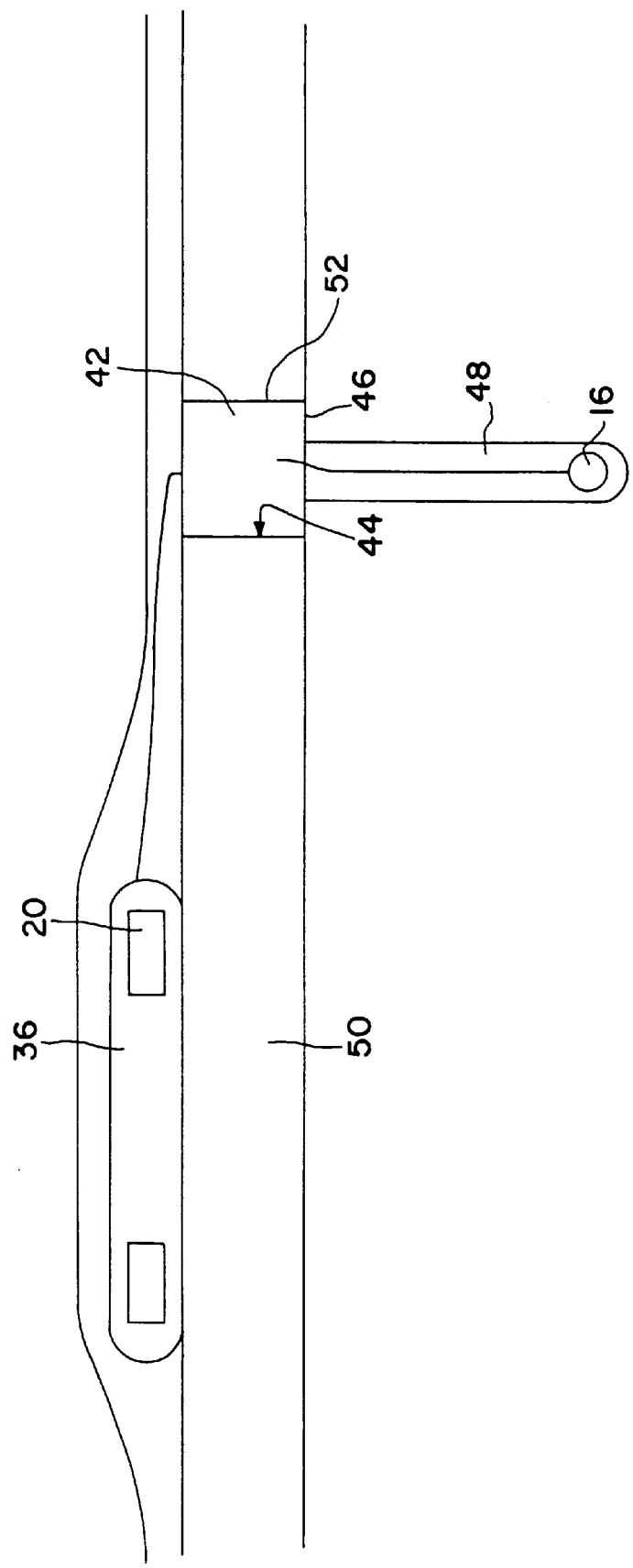
FIG. 7 is a side cross-sectional view of an alternate embodiment of the invention in place on a skull.

In another embodiment shown in FIG. 7, probe head 36 is separated from, although connected to, electronics case 42. In this embodiment, electronics case 42 is mounted through a hole 52 bored in the skull 50 and body 48 with sensor 16 is still attached to electronics case 42 in all the variants described herein. But, in this embodiment, probe head 36 with probe coil 20 is implanted underneath the patient's skin but above or in the skull 50. Probe head 36 may be attached to the patient's skull 50 by screws, adhesives or other means that will occur to those skilled in the art. Alternately, a separate hole from hole 52 may be bored into the skull 50 to receive the probe head 36. Where probe head 36 is located in the separate hole, probe head 36 may have screw threads placed on the outer edge 40 of probe head 36 and the separate hole is dimensioned to have a diameter approximately the same as the diameter of probe head 36 with threads corresponding to the threads on probe head 36. In this embodiment, to place the probe 12, the sensor 16, body 48 and electronics case 42 of probe 12 is placed through the hole 52. Probe head 36 is then attached to the skull 50 as described above.

Figure 8:
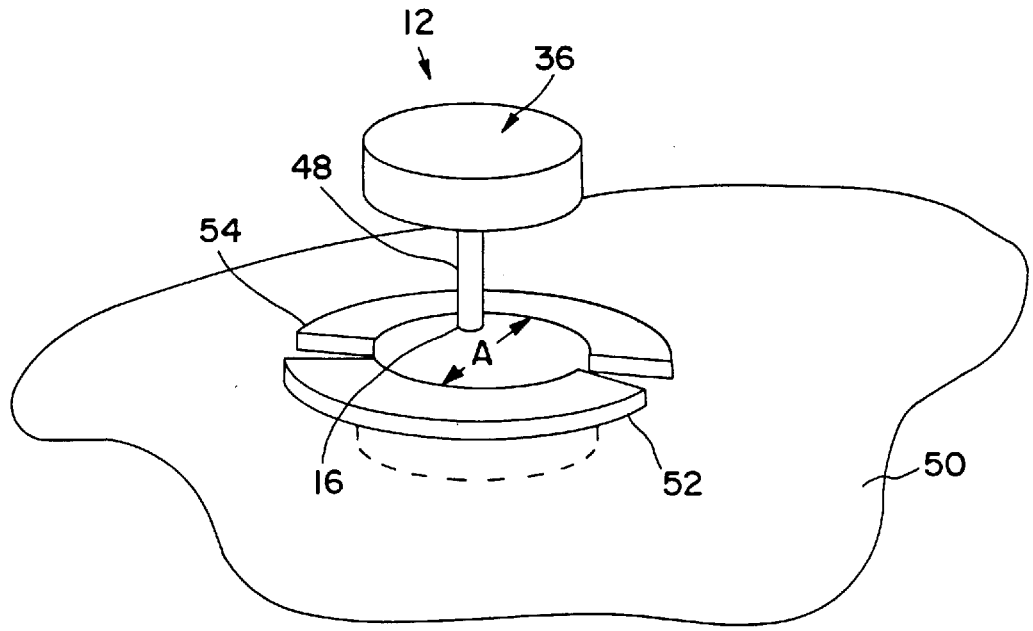
FIG. 8 is a perspective view of an alternate embodiment of the invention.
Figure 9:
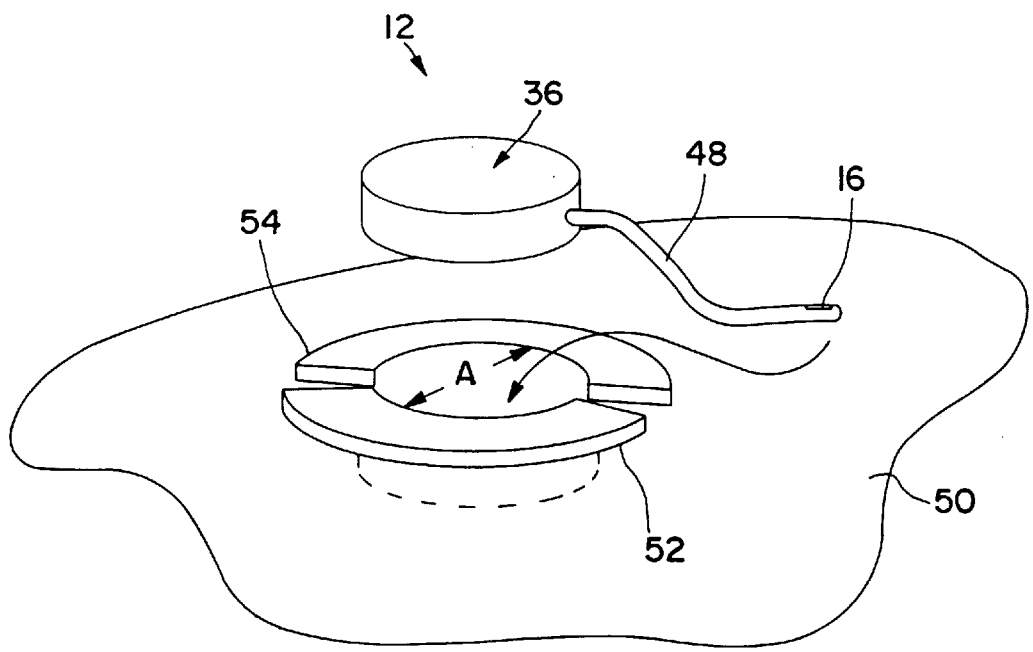
FIG. 9 is a perspective view of another alternate embodiment of the invention.

In a further embodiment shown in FIGS. 8 and 9, a burr-hole ring 54 having an opening 56 with a diameter "A" is placed in a hole 52 in skull 50. Burr-hole ring 54 may be screwed into the bone of the skull 50 or otherwise attached to the skull 50 in a fashion well known for burr-hole rings. In this embodiment, probe head 36 has a diameter about equal to the diameter "A" of the opening 56 of burr-hole ring 54. Probe head 36 is placed in the opening 56 where it may be held in place by means such as friction, body-compatible adhesive or other means that will occur to those skilled in the art.

In the embodiment of FIG. 8, the body 48 is rigid so that sensor 16 is located a fixed distance from and at a fixed relationship to the probe head 36. In the embodiment of FIG. 9, body 48 is flexible. In this embodiment, the sensor 16 is placed through the opening 56 to a desired location.

Figure 10:
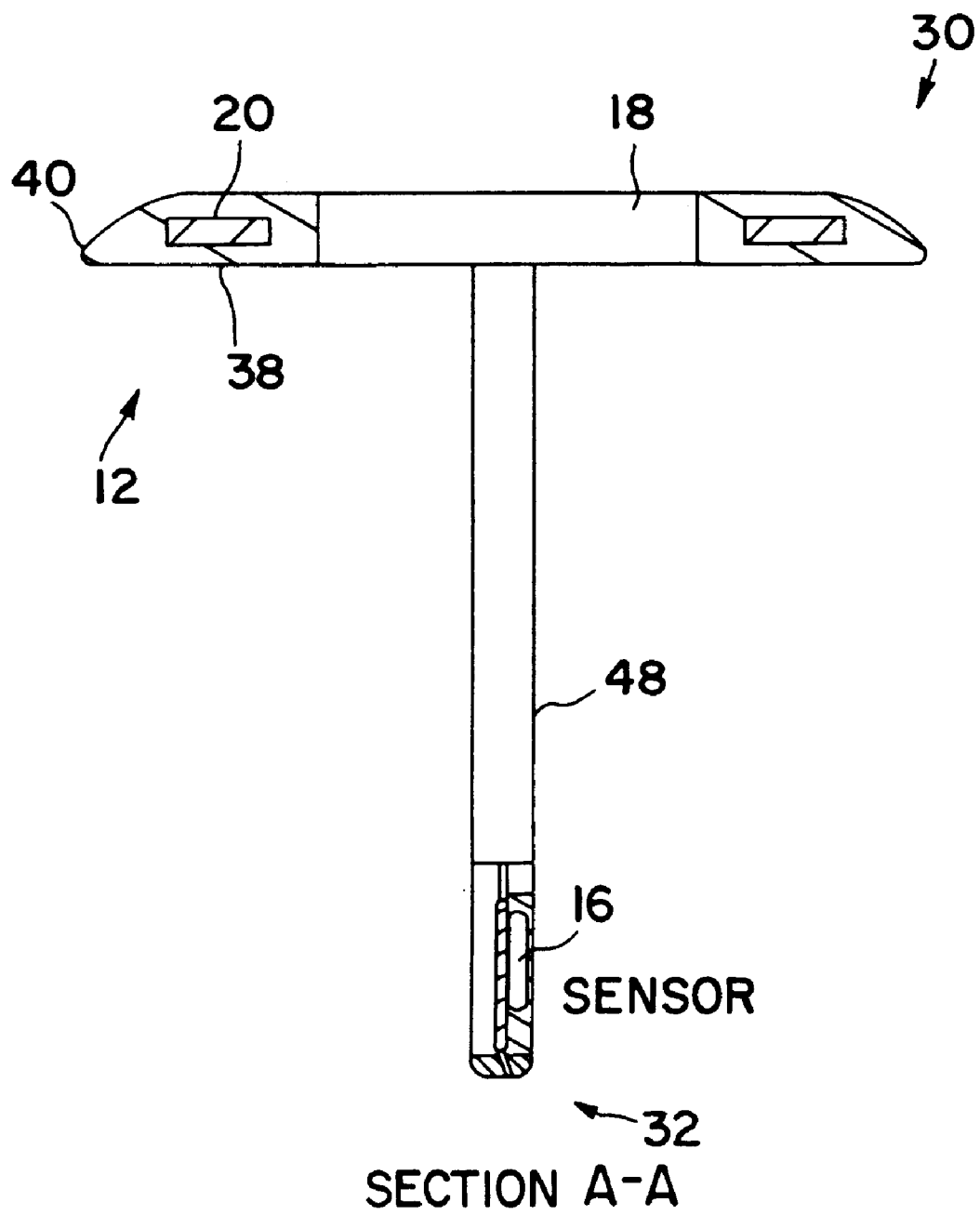
FIG. 10 is a side cross-sectional view of another alternate embodiment of the invention.

In a further embodiment shown in FIG. 10, the probe head 36 may contain all or part of the probe electronics 18. In this embodiment, there may be no need to have an electronics case 42. Therefore, the sensor 16 may be attached directly to probe head 36 through a rigid or flexible body 48. In use, a hole 52 is drilled through skull 50 and sensor 16 placed through hole 52 to a desired location. Then, probe head 36 may be attached to the skull 50 as described above.

In a variant of this embodiment, the probe head 36 may be located a distance from the hole 52. For example, the probe head may be located under the skin below the clavicle or in the abdomen at sites common for placing RF powered implantable neurological stimulators. In this embodiment, it may be necessary to use a burr-hole ring to position the body 48 at the skull 50 so that sensor 16 will not move with respect to the hole 52. Further, the probe electronics may also be located in total or in part in the body 48 in any of the embodiments described herein.

Probe electronics 18 includes sensor electronics 58 and a transmitter 60. Sensor electronics 58 is connected to sensor 16 and provides power to sensor 16, directs sensor 16 to take measurements, processes the sensed measurement signal from sensor 16 and converts the sensed signal to a digital signal. This digital signal is preferably passed to transmitter 60.

Transmitter 60 is connected to sensor electronics 58 and probe coil 20. Probe coil 20 acts as an antenna as will be explained hereafter. Transmitter 60 and probe coil 20 communicate pressure and temperature information determined by sensor 16 to the external device 14 by telemetry. Examples of telemetry systems are shown in U.S. Pat. No. 5,683,432 entitled "Adaptive, Performance-Optimizing Communication System for Communicating with an Implanted Medical Device", issued on Nov. 4, 1997 to Steven D. Goedeke, Gregory J. Haubrich, John G. Keimel and David L. Thompson, U.S. Pat. No. 5,752,976 entitled "World Wide Patient Location and Data Telemetry System for Implantable Medical Devices", issued on May 19, 1998 to Edwin G. Duffin, David L. Thompson, Steven D. Goedeke and Gregory J. Haubrich, U.S. Pat. No. 5,843,139 entitled "Adaptive, Performance-Optimizing Communication System for Communicating with an Implanted Medical Device", issued on Dec. 1, 1998 to Steven D. Goedeke, Gregory J. Haubrich, John L. Keimel and David. L. Thomson and U.S. Pat. No. 5,904,708 entitled "System and Method for Deriving Relative Physiologic Signals", issued on May 18, 1999 to Steven D. Goedeke, the teachings of which are incorporated herein in their entireties by reference. Other alternate means of communication between the probe 12 and the external device 14 include amplitude shift keying (ASK), binary phase shift key (BPSK) or quadrature phase shift key (QPSK) to name but a few choices.

Figure 11:
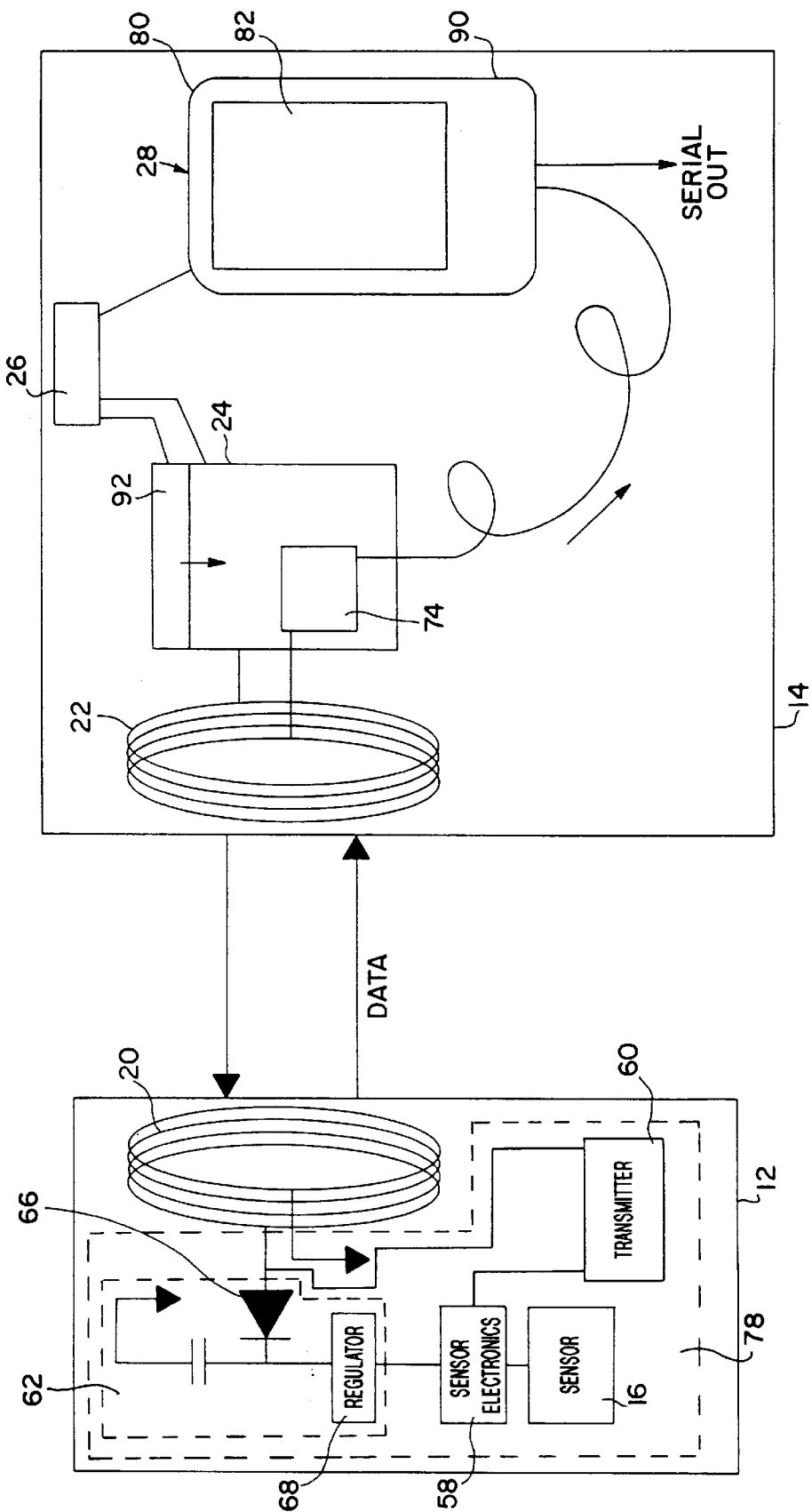
FIG. 11 is a schematic drawing of the preferred embodiment of the invention.

In addition, in the preferred embodiment, probe electronics 18 includes an AC/DC conversion system 62 (FIG. 11). Probe coil 20 is connected to AC/DC conversion system 62. Probe electronics 18 allows power to be transferred from the external device 14 to probe 12 to power probe 12 and at the same time allows probe 12 to uplink sensed physiological parameters from probe 12 to external device 14. This simultaneous power transfer and uplink of information is preferably done by a technique known as absorption modulation as is well understood in the art.

In this embodiment, AC/DC conversion system 62 includes a rectifier 66 and a regulator 68. Probe coil 20 will be inductively coupled to an external coil 22 in the external device 14 as will be explained hereafter. This inductive coupling between probe coil 20 and external coil 22 provides power to the probe coil 20. This power will be in the form of an alternating current. In the preferred embodiment, this AC current has a frequency of about 175 kHz although other frequencies may be used as desired.

Rectifier 66 is connected to probe coil 20 and converts the AC power received from the probe coil 20 to DC power. Rectifier 66 is preferably a full-wave rectifier as is well understood in the art but may be other rectification systems as is also well understood in the art. The DC power is passed through the regulator 68 that ensures a relatively constant DC level despite variations in power received from the probe coil 20 due, for example, to the relative movement of the probe coil 20 to the external coil 22. In this way, regulated DC power is provided to power the probe electronics 18.

In an alternate embodiment (FIG. 12), probe electronics 18 includes the AC/DC conversion system 62 described above and in addition includes a temporary energy source 64. Probe coil 20 is again connected to AC/DC conversion system 62. Probe coil 20 is inductively coupled to external coil 22.

In this embodiment, a temporary energy source 64 is connected to AC/DC conversion system 62. Temporary energy source 64 preferably takes the form of a rechargeable battery or a power capacitor such as a "super capacitor", having for example a small capacity such as 1 pf, although larger or smaller capacities may be used as desired.

Inductive coupling between probe coil 20 and external coil 22 provides power to the probe coil 20 and through AC/DC conversion system 62, charges up the temporary energy source 64. Temporary energy source 64 then provides the energy to power the probe electronics 18.

Probe coil 20, in the preferred embodiment (FIG. 11), also acts as an antenna connected to transmitter 60 to transmit information from sensor 16 to the external device 14. In this role, probe coil 20 acts as an antenna in addition to acting as an inductive coil for receiving power from the external device 14 as described above. As described above, probe coil 20 is a coil so that when probe coil 20 acts as an antenna, probe coil 20 is a coil antenna.

In the preferred embodiment, probe coil 20 performs both the function of inductively coupling with external coil 22 to receive power from external device and transmitting information from transmitter 60 to external device 14. In an alternate embodiment shown in FIG. 13, these two functions are separated. In this alternate embodiment, probe coil 20 performs only the function of inductively coupling with external coil 22 to receive power from external device. But, a probe antenna 70 is provided that serves the function of transmitting pressure or temperature information from the transmitter 60 to the external device 14.

Figure 12:
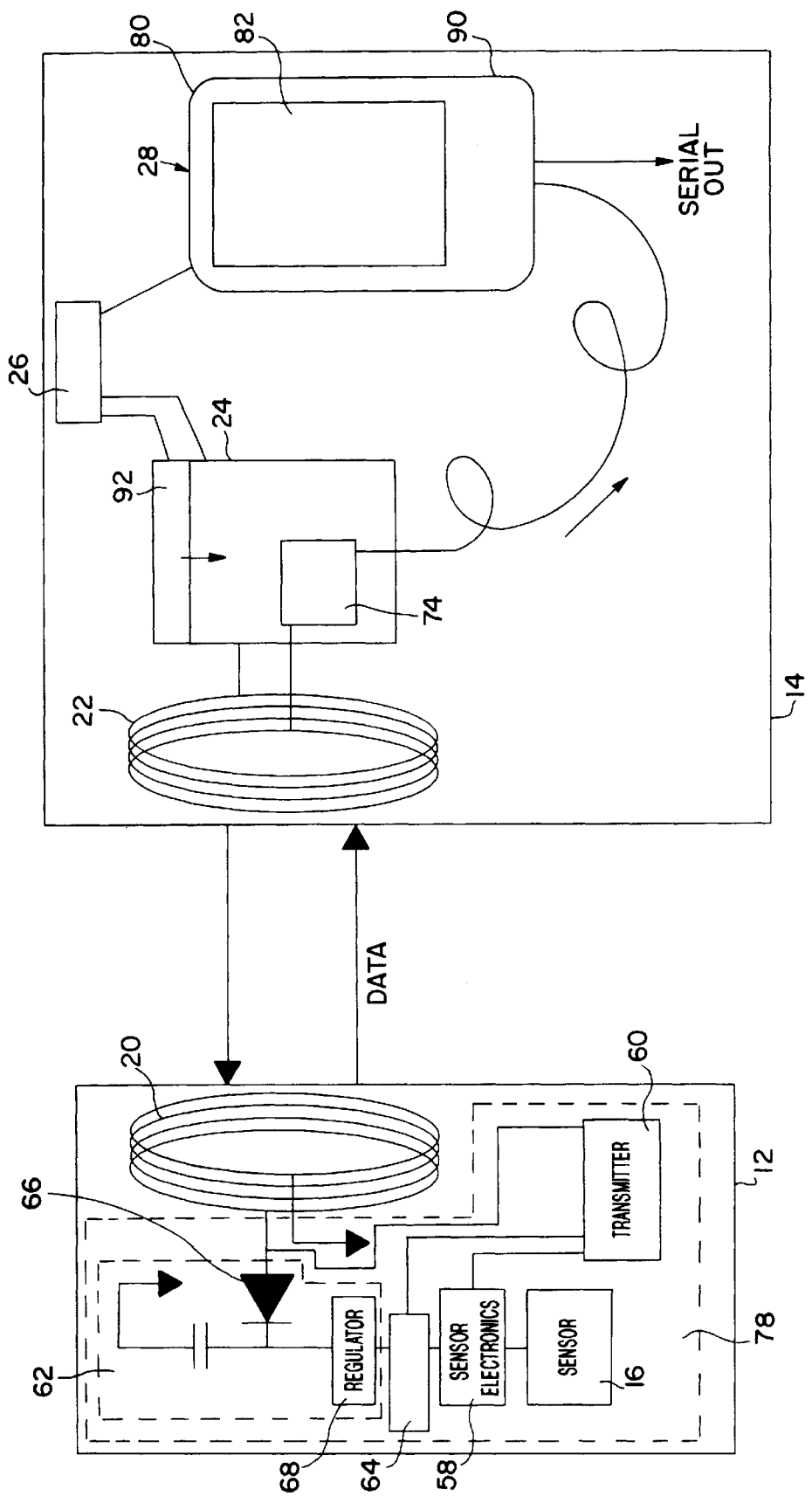
FIG. 12 is a schematic drawing of another embodiment of the invention.
Figure 14:
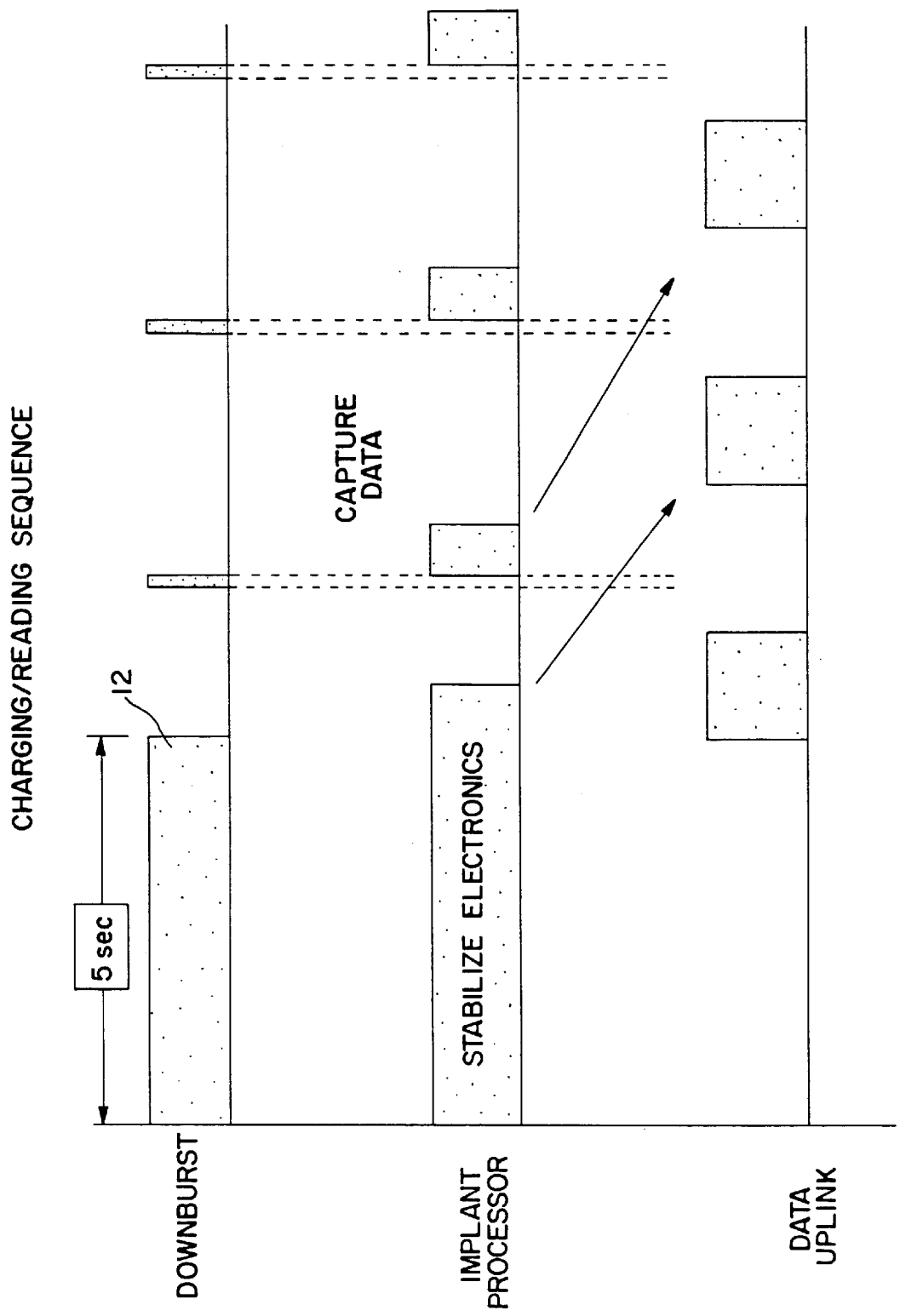
FIG. 14 is a chart showing the charging and transmitting sequence of one embodiment of the invention.

In the embodiment of FIG. 12, as shown in FIG. 14, when probe coil 20 is inductively coupled to external coil 22, probe coil 20 receives a downburst of energy 72 from the external device 14 through the external coil 22. The downburst of energy 72 preferably lasts for a specified time period to allow the temporary energy source 64 to be charged, for example, about 5 seconds, although more or less time may be used as desired. This downburst of energy 72 is converted to a regulated DC voltage by rectifier 66 and regulator 68 and charges the temporary energy source 64 to provide temporary energy to the probe electronics 18 as described above.

When the probe coil 20 is inductively coupled to the external coil 22 and the probe 12 is receiving power from the external device 14 or after the temporary energy source 64 is charged, sensor electronics 58 directs sensor 16 to sense the pressure or temperature and communicate the sensed pressure or temperature to the sensor electronics 58. Sensor electronics 58 processes the sensed pressure or temperature information and passes it to the transmitter 60 where the pressure or temperature information is converted into a form capable of being sent via telemetry from the transmitter 60 to the external device 14. The pressure or temperature information is then sent from the transmitter 60 and either the probe coil 20 acting as an antenna or the probe antenna 70, to the external device 14. External device 14 receives the transmitted pressure or temperature information through the external coil 22 acting as an antenna or the external device antenna 94, and a receiver 74, preferably located within external device 14.

This process of sensing pressure or temperature and transmitting it to the external device 14 may be continued for as long as the probe 12 receives power from the external device 14 or as long as the temporary energy source 64 has power or for a lesser time if desired. If sufficiently many occurrences of sensing pressure or temperature and communicating the sensed pressure or temperature are desired so that the power capacity of the temporary energy source 64 is or will be exceeded, power may again be downloaded from the external device 14 as described above. As a result, the temporary energy source 64 will be recharged and the sensing and transmitting process continued as described above.

The preferred embodiment of probe 12 is a passive system without a long-term power source on the probe 12. As a result, probe 12 is a relatively low-cost device for measuring and communicating pressure or temperature. This embodiment allows a "real time" snapshot of the pressure or temperature.

Figure 15:
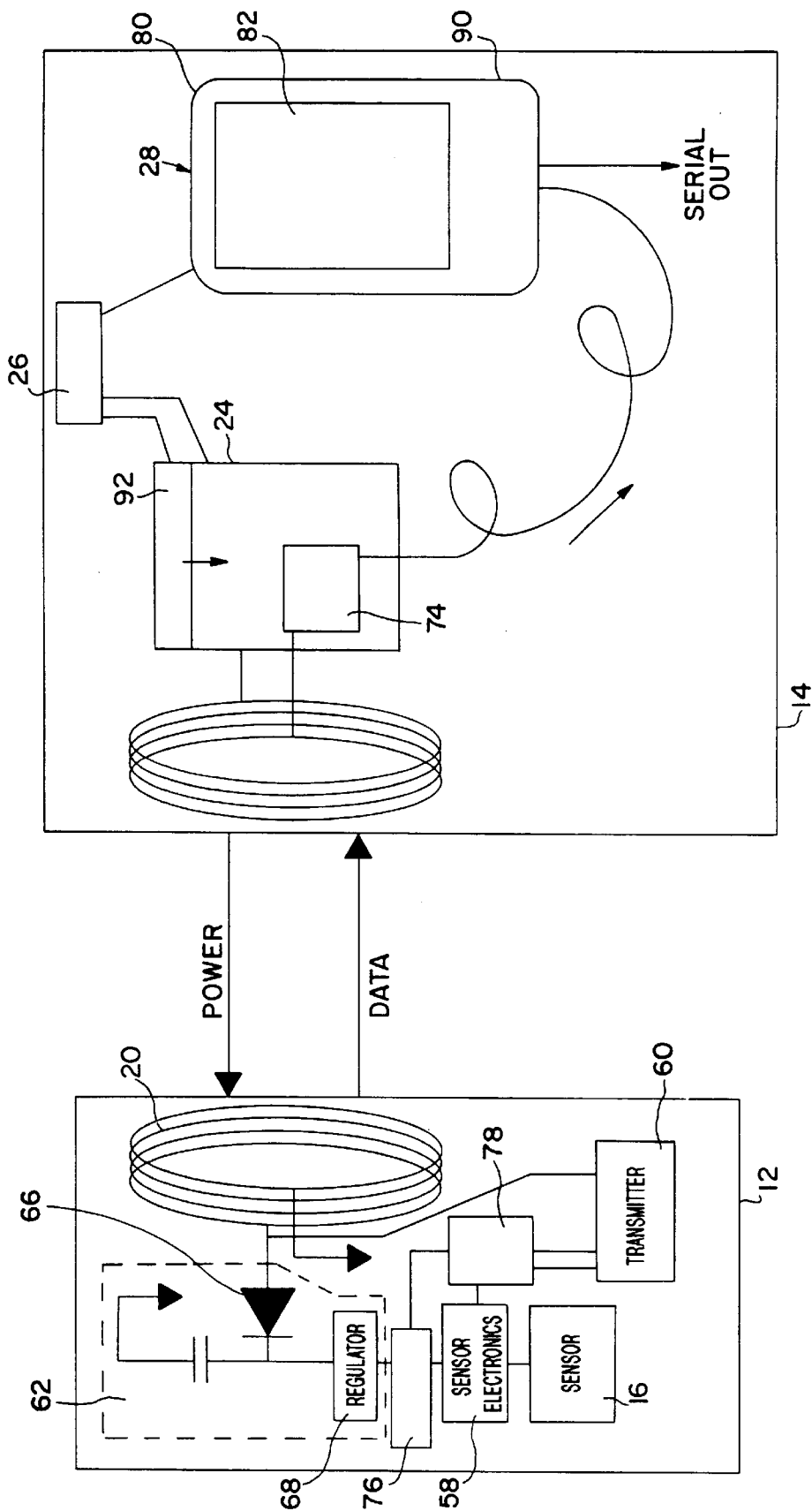
FIG. 15 is a schematic drawing of another embodiment of the invention.

Alternately, as shown in FIG. 15, a long-term power source 76 may be provided to power the probe electronics 18. Long-term power source 76 may take the form of a battery that may or may not be rechargeable or a power capacitor such as a "super-capacitor" as is well understood in the art. Long-term power source 76 must have a capacity sufficient to power the probe 12 for a relatively long time. Where the long-term power source 76 is used, the temporary energy source 64 is replaced with the long-term power source 76. Where a storage device 78 is present, as will be explained hereafter, long-term power source 76 may also provide power to storage device 78 as well.

In the preferred embodiment (FIG. 11), external device 14 includes an external coil 22, external electronics 24, a power source 26, and a user communication system 28. Power source 26 provides power to operate the external electronics 24 and user communication system 28 and provides power to external coil 22 that will be passed to probe 12 through inductive coupling with probe coil 20. Power source 26 may be either a battery or ordinary line current that has been adapted to provide power by such means as rectifying and filtering line AC power to produce a DC voltage as is well understood in the art.

External electronics 24 preferably contains a receiver 74 although the receiver 74 may be a separate component connected to the external device 14. Receiver 74 receives and processes the pressure or temperature information transmitted by transmitter 60 and received by external coil 22 acting as an antenna.

User communication system 28 is connected to receiver 74. User communication system 28 preferably includes a display system 80 that displays or otherwise communicates the pressure or temperature information received by receiver 74 to a user. User communication system 28 may include a display screen 82 that displays the pressure or temperature information to the physician or other user. Alternately, user communication system 28 may pass the pressure or temperature information from the external device 14 to an external computer 84, including a handheld personal digital assistant (PDA), the internet or through a modem by direct connection 86 or through telemetry 88 as is well understood in the art. Computer 84 can display the pressure or temperature information on its display screen 82, record the information or further process the information. If the information is passed through the internet or through a modem, the information may be remotely used, processed or displayed as desired.

User communication system 28 may also include an alarm 90 that is part of the external device 14 or the external computer 84 that is triggered to alert the user to a pressure or temperature that is outside of a pre-determined range. The alarm 90 can also take the form of an audible or visible warning such as a warning chime or a flashing visual display panel, a physical warning such as a vibrating alarm or other means of alerting the user or emphasizing the status as will occur to those skilled in the art.

External device 14 also preferably includes a barometer 92. Barometer 92 measures the atmospheric pressure. This measured atmospheric pressure is then subtracted from the pressure measured by sensor 16 and transmitted from probe 12 to external device 14 to produce the "gauge" pressure. This "gauge" pressure is independent of the ambient atmospheric pressure, which is influenced by weather systems and altitude.

In the preferred embodiment, external coil 22 serves both to couple with the probe coil 20 to provide power to the probe 12 and as an antenna to receive information transmitted by probe 12 from transmitter 60. As such, external coil 22 is connected to receiver 74.

Alternately, an external device antenna 94 may be present, separate from external coil 22. In this embodiment, external device antenna 94 is connected to receiver 74 and communicates with probe antenna 70 or probe coil 20 to receive information transmitted from transmitter 60. In this embodiment, external coil 22 is not connected to receiver 74.

To use the device 10 to measure a parameter of the brain such as CSF fluid pressure, the first step is to expose the skull and drill a hole 52 in the skull 50. The probe 12 is then implanted as described above. Thereafter, the patient's skin is closed so that the probe 12 is entirely contained under the patient's skin.

The external device 14 is brought near the probe 12 so that the probe coil 20 is inductively coupled to the external coil 22 and power is transferred from the external device 14 to the probe 12.

The hole 52 is then sealed with the probe 12 in place. Thereafter, the patient's skin is surgically closed over the probe 12 where the wound will heal. This will seal the probe 12 underneath the patient's skin.

When a measurement of a physiological parameter is desired, the external device 14 is placed with its external coil 22 over the probe coil 20. The probe 12 is powered by transmitting a downburst of energy 72 from the external device 14. In the preferred embodiment, the initial downburst of energy 72 after power-up lasts about 5 seconds. This allows the probe electronics 18 to stabilize and set up such things as internal clocks, etc. Subsequent downbursts of energy 72 are preferably about 2 ms long.

In the preferred embodiment, the probe 12 does not have an on-site battery. Therefore, on power-up the probe electronics 18 performs an autocalibration operation to ensure that the physiological measurements by sensor 16 will fall within the range of the probe electronics 18. Whenever the falling edge of the downburst of energy 72 is detected, the probe 12 uplinks its sensed physiological measurements to the external device 14. The uplink continues for as long as the external device 14 sends downbursts of energy 72 to the probe 12. The frequency of uplink is controlled by the external device 14 and cannot exceed the rate of downburst of energy 72. It is also possible to periodically uplink the stored calibration coefficients to the external device 14 or to uplink the stored calibration coefficients to the external device 14 with every uplink of sensed physiological parameters.

In the preferred embodiment, each uplink of the sensed physiological measurements is transmitted from probe 12 to external device 14 multiple times, for example thrice, to compensate for telemetry or processing errors. In a continuous mode, when the external device 14 intermittently sends downbursts of energy 72 to provide essentially continuous power to probe 12 and receives uplinked physiological parameter measurements.

In addition, as explained above, calibration coefficients for sensor 16 may be stored in the probe 12 in the probe electronics 18, storage device 78 or microprocessor 102. Where these calibration coefficients are stored in probe 12, these coefficients may be uplinked from the probe 12 to the external device for the purpose of post-measurement processing to achieve to achieve an accurate report of the physiological parameters measured by sensor 16. These coefficients may be uplinked to external device 14 when probe 12 is first powered up or may be uplinked with every uplink of sensed physiological parameters.

Further, data such as the serial number or model number of the probe 12 may be stored in probe 12 in the probe electronics 18, storage device 78 or microprocessor 102 or in the external device 14. Where such serial number or model number is stored in probe 12, this information may be uplinked to external device 14 when probe 12 is first powered up or may be uplinked with every uplink of sensed physiological parameters.

Figure 16:
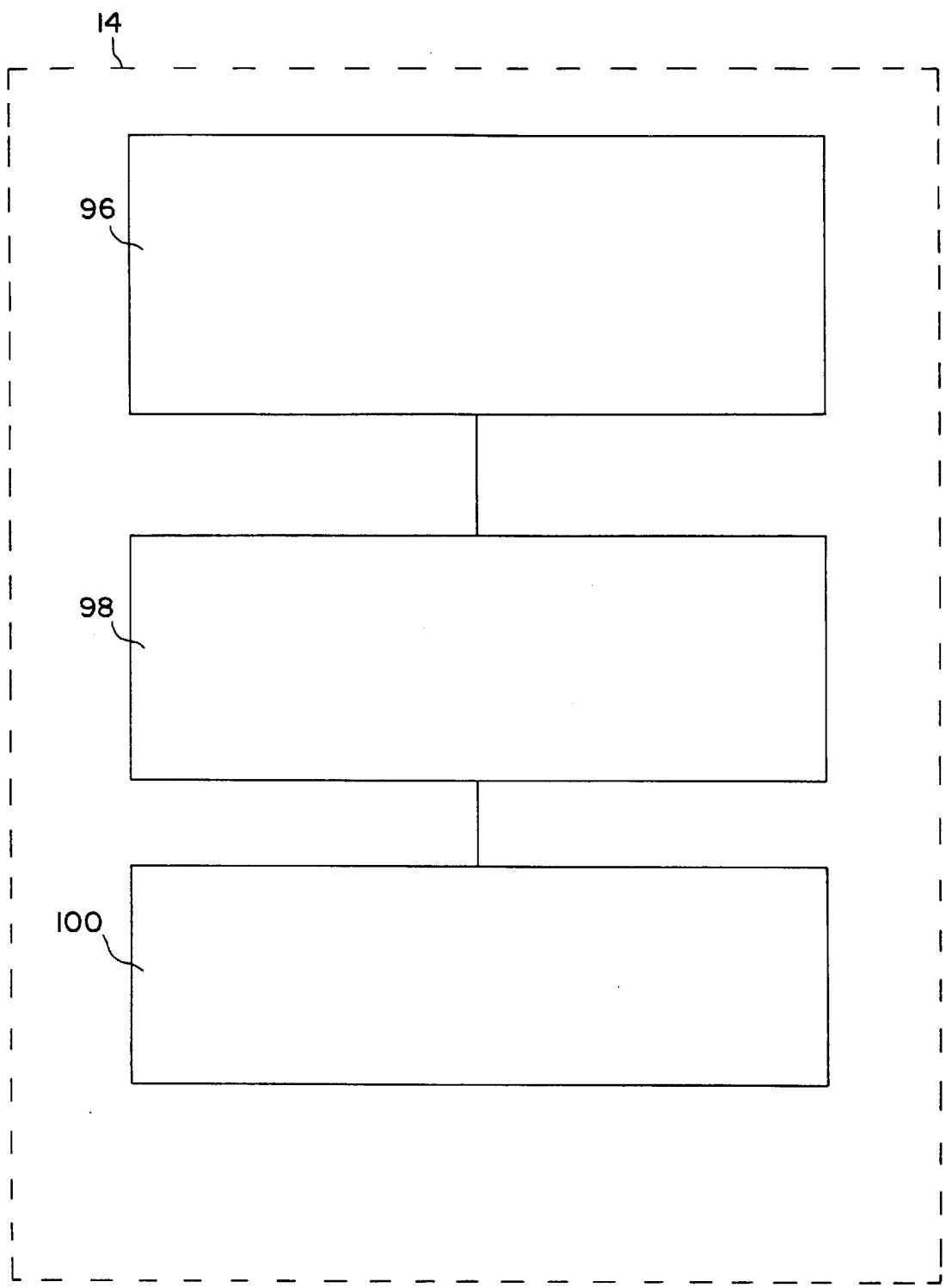
FIG. 16 is a block diagram of an alternate embodiment of the invention.

In the preferred embodiment, external device 14 is a single unit that includes the components of an external coil 22, external electronics 24, a power source 26, user communication system 28 and an external device antenna 94, if present. However, external device 14 may be two or more separate devices. For example, as shown in FIG. 16, one device 96 may provide power to the probe 12 through inductive coupling between the probe coil 20 and external coil 22, a second device 98 may receive the pressure or temperature information transmitted by transmitter 60 and a third device 100 may display the pressure or temperature information received by the second device 98.

In the preferred embodiment where probe 12 includes a passive system 24, it is critical that probe coil 20 and external coil 22 be coupled to allow power to be passed from the external device 14 to the probe 12 and for pressure or temperature information to be passed from probe 12 to external device 14. It may be desirable to have an audible confirmation that probe coil 20 and external coil 22 are coupled. This may be accomplished by probe 12 uploading a signal to external device 14 indicating that probe coil 20 and external coil 22 are inductively coupled. This signal may be used by the external device 14 to trigger an audible signal indicating that the probe 12 and the external device 14 are inductively coupled.

Alternately, the loading of the external coil 22 caused by the inductive coupling with the probe coil 20 can be detected by the external device 14 and used to determine coupling efficiency. This loading can be detected by monitoring the power passed through the external coil 22. As the inductive coupling between the external coil and probe coil 20 increases, the power passing through the external coil 22 to the probe coil 20 will increase. By monitoring this power and comparing instantaneous power measures, trends in power transmission (i.e., increasing or decreasing) or a relative maximum power transmission amount may be determined. This information can be used to determine whether increasingly efficient coupling positions between external coil 22 and probe coil 20 are being reached or that the optimum coupling position has been reached.

Figure 17:
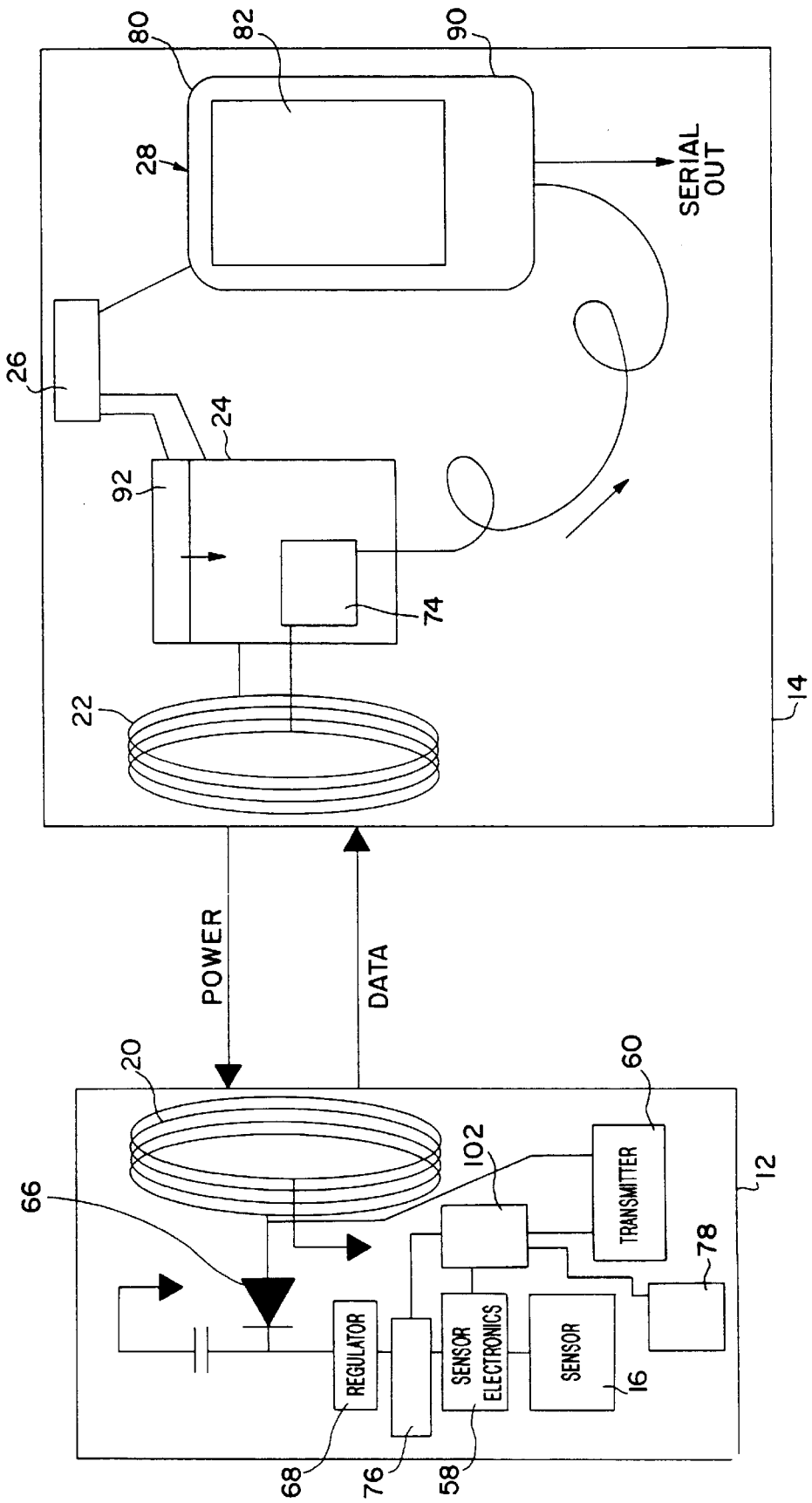
FIG. 17 is a schematic drawing of another embodiment of the invention.

Further, it may be desirable to store sensed pressure or temperature information from the sensor 16 to be transmitted from transmitter 60 at a later time. This may be accomplished by having a storage device 78 attached to sensor 16 and transmitter 60 (FIG. 17). Storage device 78 may be of the type disclosed in U.S. Pat. No. 5, 817,137 entitled "Compressed Patient Narrative Storage In and Full Text Reconstruction from Implantable Medical Devices", issued on Oct. 6, 1998 to William F. Kaemmerer or U.S. Pat. No. 5,549,654 entitled "Interactive Interpretation of Event Markers in Body-Implantable Medical Devices" issued to Richard M. Powell on Aug. 27, 1996, both assigned to the assignee of the present application, the teachings of which are incorporated herein by reference in their entirety.

Storage device 78 may be located in probe head 36, electronics case 41 or body 48 or may be located separate from but electrically connected to the probe 12. For example, storage device 78 may be located near the clavicle in a manner similar to the placement of the Reveal® cardiac recording device manufactured and sold by Medtronic, Inc.

of Minneapolis, Minnesota. Further, storage device 78 may be directly connected to probe 12 by wires, through the "body bus" communication system described above or other similar communication means.

In this embodiment, probe 12 requires a long term power source 76 to provide power to the sensor 16, sensor electronics 58 and the storage device 78. Sensor electronics 58 would periodically direct sensor 16 to sense the pressure or temperature. Alternately, sensor electronics 58 could be directed from a signal from the external device 14 to direct sensor 16 to sense pressure or temperature information.

In either case, the sensed pressure or temperature would then be communicated to the storage device where it would be stored. Then, either periodically or when an inquiry is made from the external device 14, pressure or temperature information would be uploaded from the storage device 78 through the transmitter 60 to the external device 14 as described above.

Figure 13:
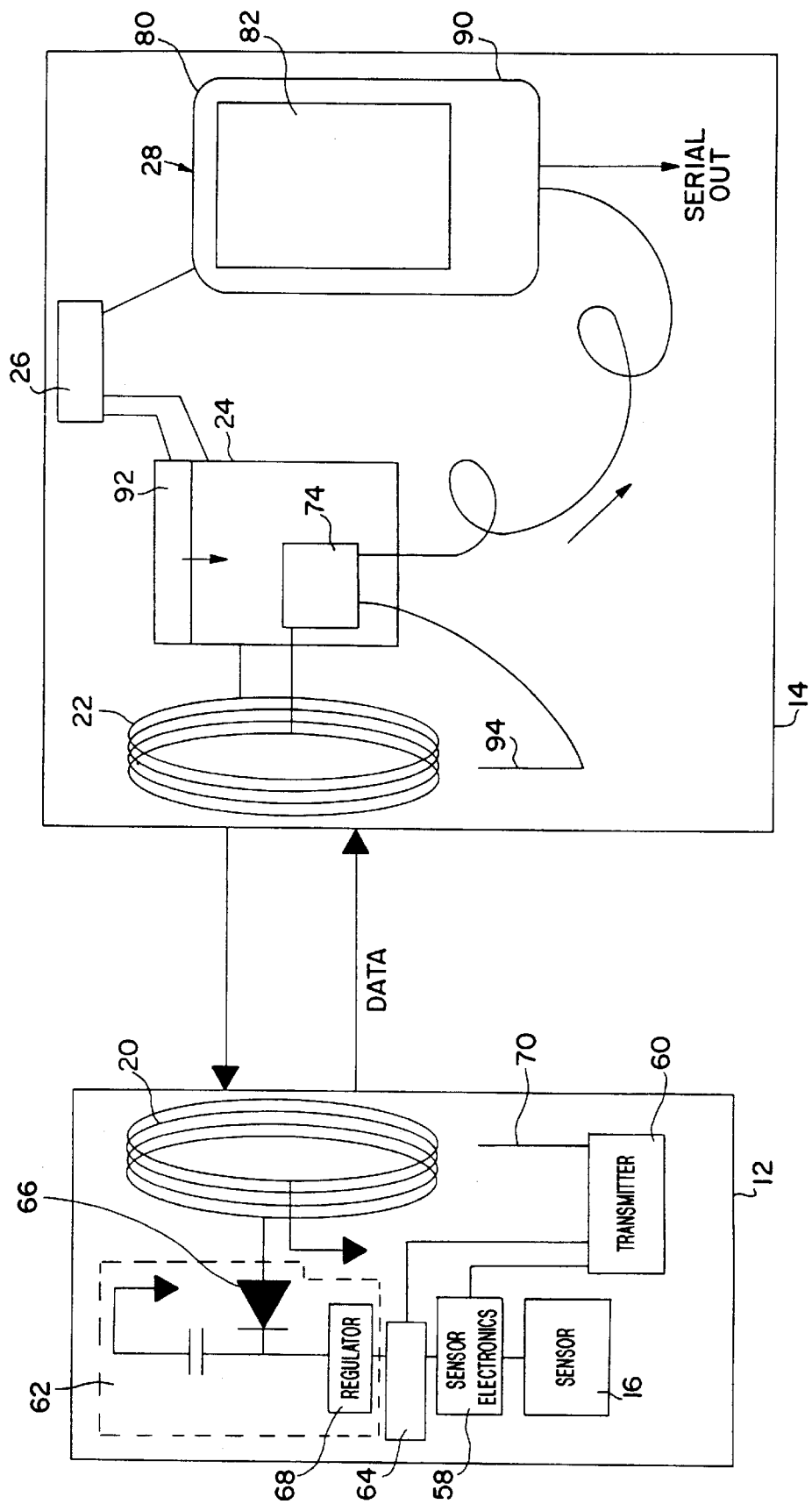
FIG. 13 is a schematic drawing of another embodiment of the invention.

In an alternate embodiment (FIG. 18), sensor electronics 28 and storage device 78 may be connected to a microprocessor 102 as shown in FIG. 13. In this embodiment, pressure or temperature measurements may be processed by microprocessor 102 before being stored in storage device 78. Alternately, microprocessor 102 may take a series of stored measurements from storage device 78 and process the series, as for example, to produce a running average pressure or temperature. Such processed information may by transmitted from probe 12 to external device 14 at the time of the processing or may be stored in storage device 78 to be transmitted to external device 14 at a later time.

The sensed pressure or temperature information may also be used to control a CSF shunt drainage system such as that described above. In this embodiment, shown schematically in FIG. 18, the sensed pressure, or temperature information if desired, is used to activate a control device 104.

Figure 18:
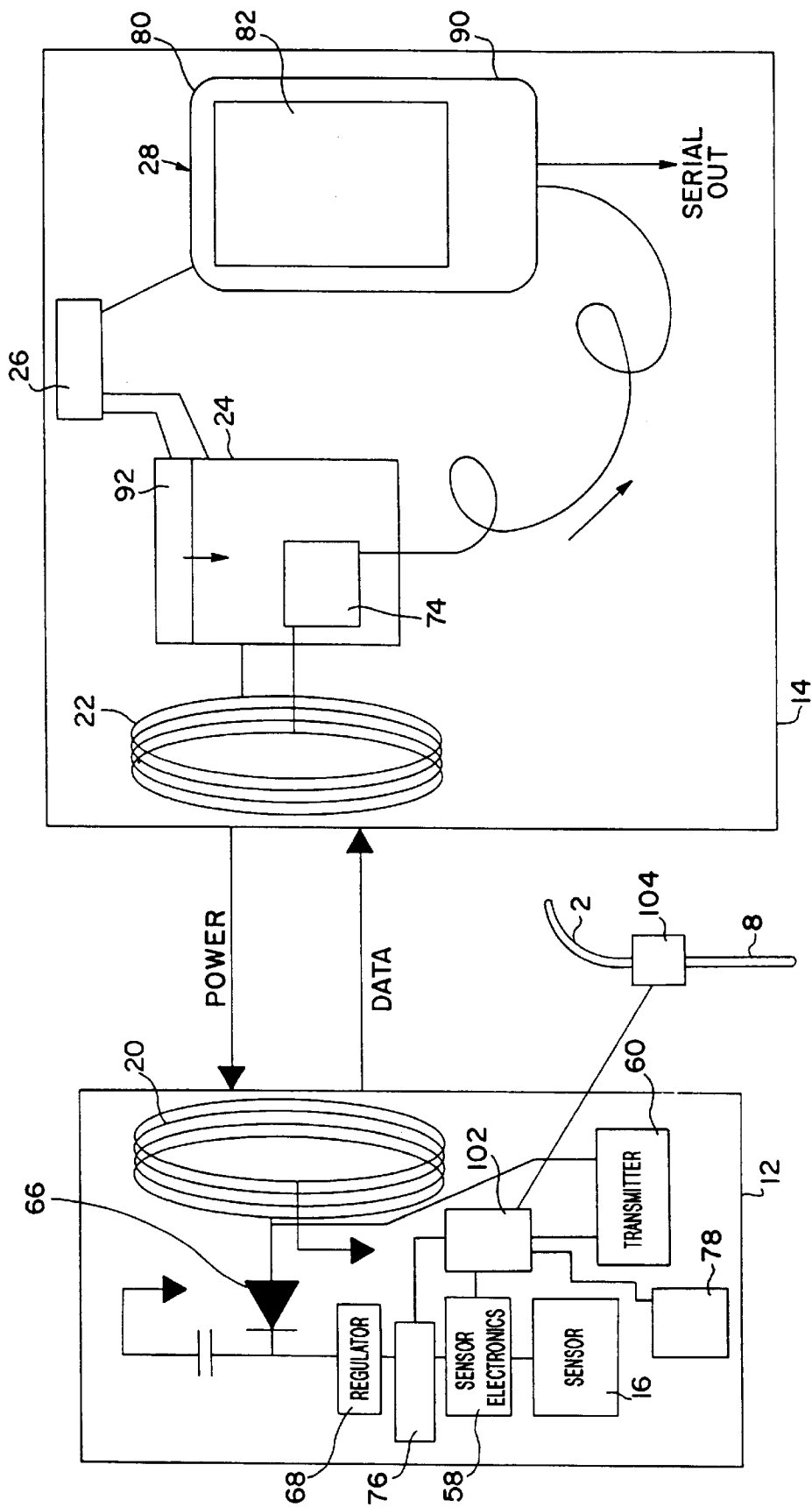
FIG. 18 is a schematic drawing of another embodiment of the invention.

In the embodiment of FIG. 18, a drainage catheter 2 is placed in the ventricle 4 of a patient, coupled to the control device 104. The control device 104 is preferably connected to a peritoneal or atrial catheter 8 although the control device 104 could be connected to a drainage bag. Control device 104 may be a pump or a valve connected between the drainage catheter 2 and the peritoneal or atrial catheter 8 or drainage bag. Where the control device 104 is a pump, the pump pumps CSF fluid from the ventricle 4 to the peritoneal or atrial catheter 8 where it is absorbed into the body or into a drainage bag. Where the control device 104 is a valve, the valve, when open, allows CSF fluid to drain from the ventricle 4 through the peritoneal or atrial catheter 8 or into the drainage bag.

In the embodiment shown, the control device 104 is connected to microprocessor 102 so that microprocessor 102 controls whether the pump pumps CSF fluid or the valve is open to allow the drainage of CSF fluid.

In use, where microprocessor 102 has determined that the CSF pressure sensed by sensor 16 exceeds a predetermined level, microprocessor 102 activates the control device 104 to either pump CSF fluid or to open the valve to allow the excess CSF fluid to drain from the patient's ventricle. When the microprocessor 102 has determined that the CSF pressure has fallen to an acceptable level, microprocessor 102 causes control device 104 to either cease pumping CSF fluid or closes the valve so that CSF ceases to drain through the valve.

The control device 104 may also control the operation of an adjustable subcutaneously implantable fluid flow valve in a CSF shunt system. Such a device is the Strata® Valve Adjustble Valve manufactured and sold by Medtronic—PS Medical of Goleta, California and as disclosed in U.S. Pat. No. 5,637,083 entitled "Implantable Adjustable Fluid Flow Control Valve", issued on Jun. 10, 1997 to William J. Bertrand and David A. Watson. Such an adjustable valve is useful in a physiological shunt system for controlling the flow of fluid from one part of the body to another such as from the patient's ventricle to the patient's peritoneal cavity or atrium of the heart. The control device 104, for example, controls the movement of an external or percutaneously-applied magnetic field, to cause the valve to provide a variety of pressure or flow characteristics.

In a variant of the embodiment using the control device 104 to control a valve or pump, the control device may also control another medical device such as a pacemaker, neurological electrical stimulator or a drug pump. With these medical devices or with this CSF shunt drainage system described above, in addition to activating control device 104 when the parameter of interest exceeds certain limits, the control device 104 can be activated anytime the parameter of interest is outside of any predetermined limits and de-activated when the parameter is within the predetermined limits. In addition, rather than control device 104 just responding in a binary fashion to the sensed parameter of interest, control device 104 can respond in a proportional, formulaic, logarithmic, geometric, exponential or predetermined response or inverse to any of these response to the sensed parameter. In this embodiment, a value representing the sensed parameter itself may be used to determine the response of the control device 104.

In use, sensor 16 is preferably placed in or in contact with the parenchyma or ventricles of the brain where pressure or temperature information may be sensed. Alternately, sensor 16 may be placed in or in contact with or in the spinal column, organs of the body such as the liver, kidneys, the heart, the bladder, to name but a few organs that will occur to those skilled in the art, tumors or growths, body tissue, joints, cavities, sinuses or spaces between organs or tissue.

In the preferred embodiment, probe 12 has either a pressure or a temperature sensor 16. However, probe 12 may also have both a pressure and a temperature sensor 16. Further, although sensor 16 has been described as a sensor to sense pressure or temperature, sensor 16 may also be a sensor that senses partial oxygen pressure ($PO_2$), mixed venous oxygen saturation ($SVO_2$), blood glucose and pH, to name but a few possibilities that will occur to those skilled in the art. Where sensor 16 senses parameters other than pressure or temperature, probe may include such as sensor in addition to or in any combination with the sensors to sense pressure or temperature. As a result, sensor 16 may sense more than one parameter either sequentially or simultaneously.

In addition, in the preferred embodiment, the probe electronics 18 are located in the electronics case 42. In an alternate embodiment, the probe electronics 18 may be located in the body 48 or in the probe head 36.

One advantage of the device 10 described herein is that long-term monitoring of a physiological parameter can be conveniently performed without risk of infection since the organ or tissue of interest, for example, the brain, is exposed only once during implantation. Thereafter, the probe 12 is encased within the skin of the patient where it can measure and communicate the physiological parameter of interest.

A further advantage of the present invention, when in the form of a pressure sensor, over prior pressure sensors is that the pressure sensor is placed directly in the brain without any tube attachment to the external world. Further, the device in the preferred embodiment does not have an on-site battery. Therefore, the probe 12 must run a start-up sequence each time power is transferred to the probe 12. In the present invention, this start-up sequence involves running an auto-calibration algorithm. This auto-calibration algorithm ensures that the pressure measurements received from the sensor 16 will always be within the desired range of the probe electronics 18.

Figure 19:
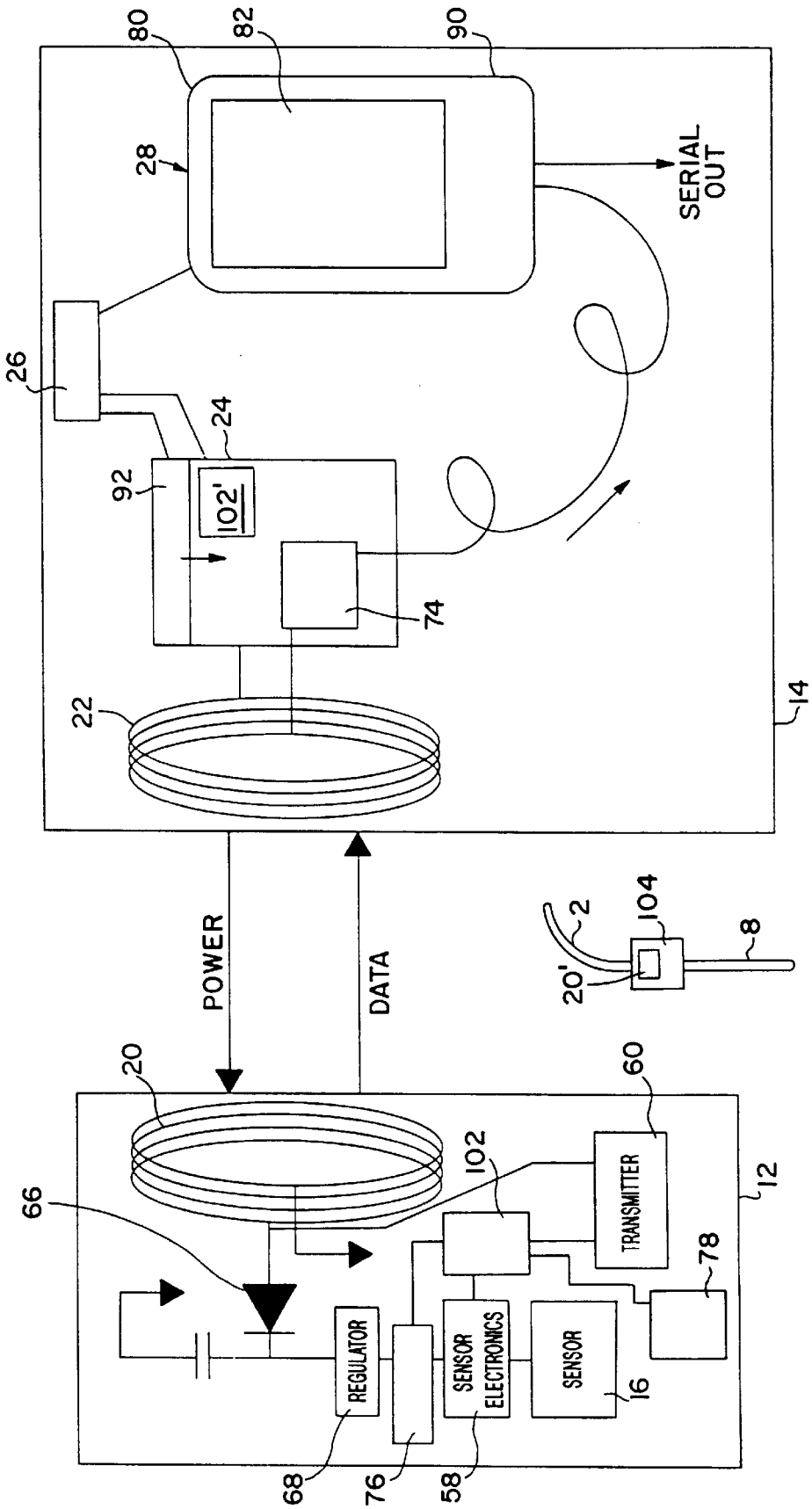
FIG. 19 is a schematic drawing of another embodiment of the invention.

In an alternate embodiment (FIG. 19), probe 12, external device 14, drainage catheter 2, atrial catheter 8 and control device 104 are as described above in connection with the embodiment of FIG. 18 with the following exception. In this embodiment, control device 104 is controlled by external device 14 so that external device 14 controls whether the pump pumps CSF fluid or the valve is open to allow the drainage of CSF fluid. In this embodiment, external device has a microprocessor 102' similar to microprocessor 102 for processing the physiological parameter information sensed by sensor 16 and control device 104 has an antenna 20' similar to probe coil 20 for receiving control signals from external device 14 through external coil 22. In the embodiments of either FIG. 18 or 19, sensor 16 may be located remotely from probe 12.

In use, sensor 16 senses pressure as described above. This pressure information may either be processed by microprocessor 102 on probe 12 or may be passed from probe 12, in whole or after partial or complete processing by microprocessor 102, to external device 14. External device 14, through microprocessor 102', then determines whether the CSF pressure sensed by sensor 16 exceeds a predetermined level. If the CSF pressure exceeds a predetermined level, external device 12 activates the control device 104 to either pump CSF fluid or to open the valve to allow the excess CSF fluid to drain from the patient's ventricle. When the external device 12 has determined that the CSF pressure has fallen to an acceptable level, external device 12 causes control device 104 to either cease pumping CSF fluid or closes the valve so that CSF ceases to drain through the valve.

Figure 20:
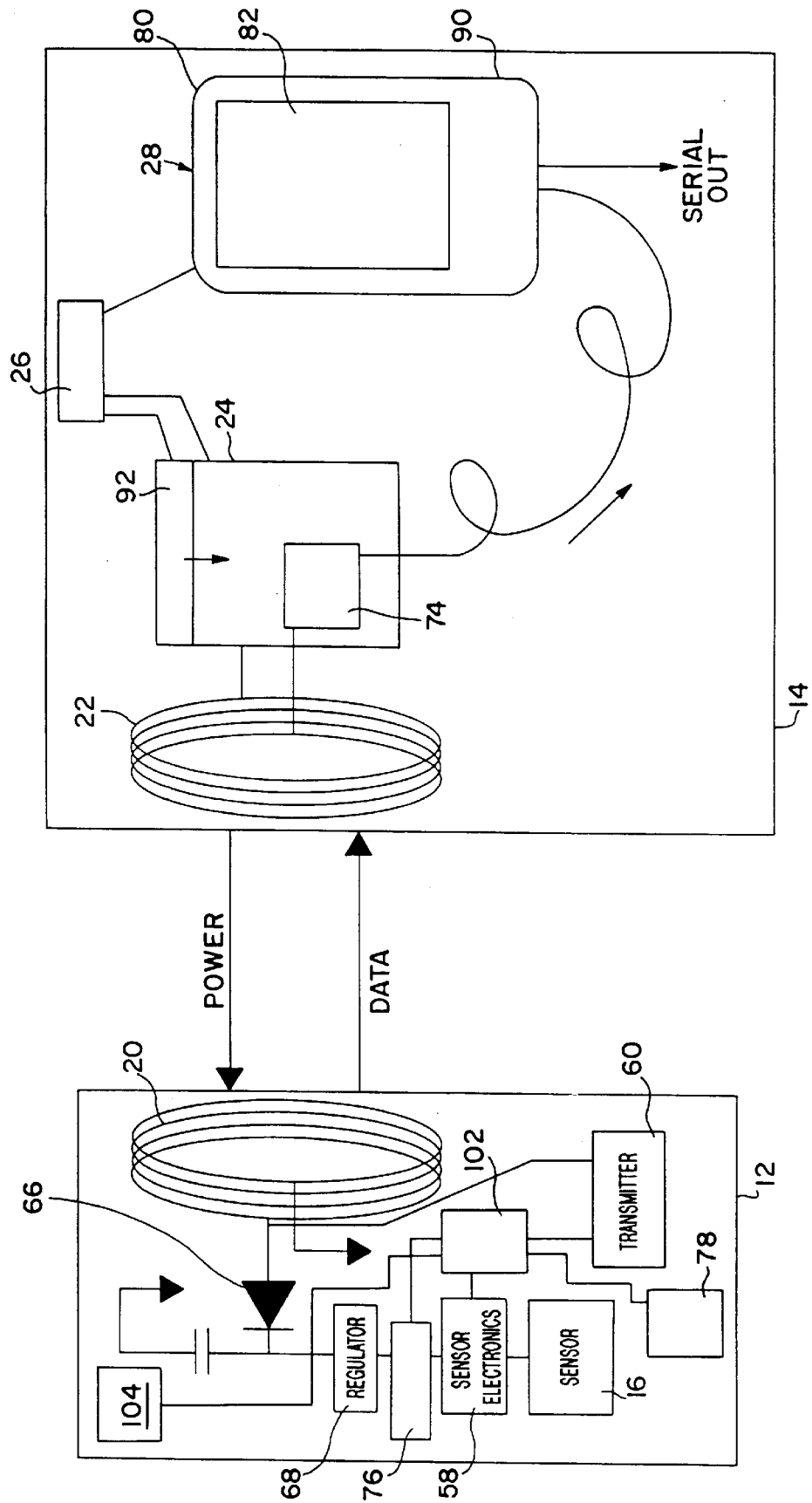
FIG. 20 is a schematic drawing of another embodiment of the invention.

In a further alternate embodiment (FIG. 20), external device 14, drainage catheter 2, atrial catheter 8 and control device 104 are as described above in connection with the embodiments of FIGS. 18 and 19 with the following exception. In this embodiment, the electronics of probe 12 are combined with control device 104. Sensor 16 is preferable located separately from probe 12 but is not required to be separated. Control device 104 may either be controlled by microprocessor 102, microprocessor 102' or a combination of microprocessors 102 and 102' as described above.

Figure 21:
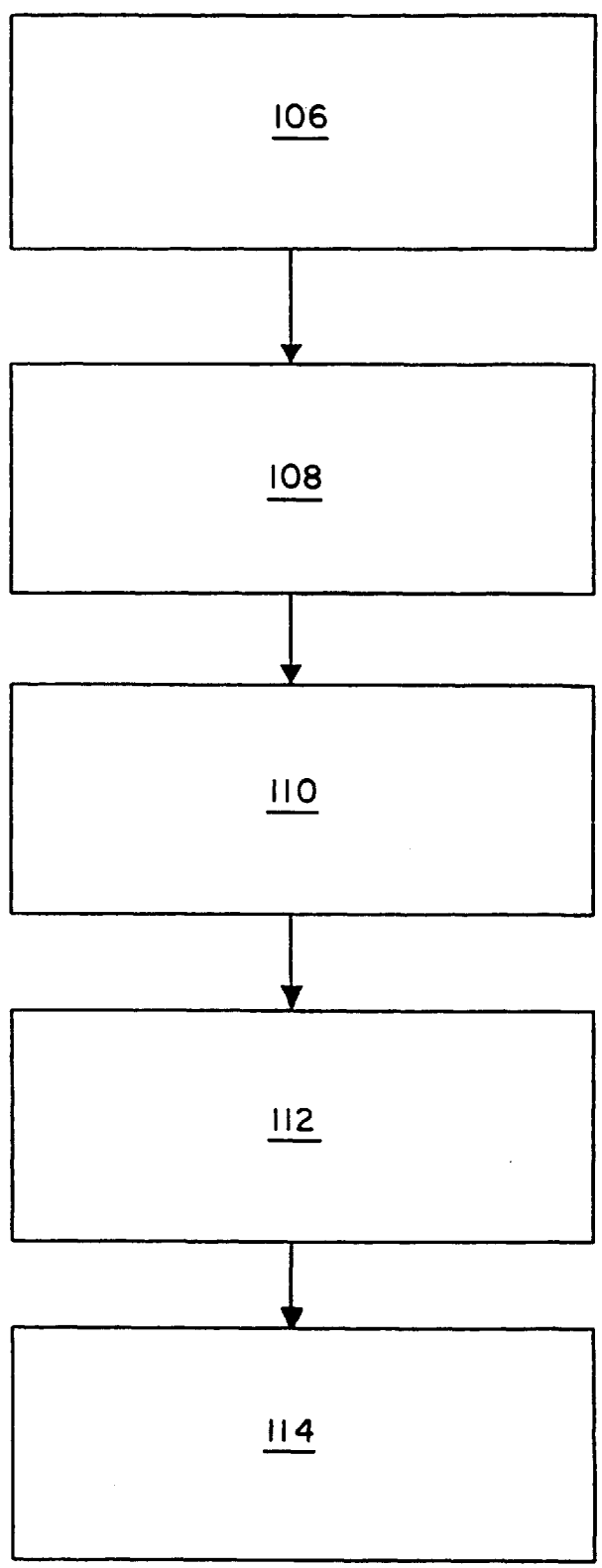
FIG. 21 is a flow chart showing one embodiment of the method of the invention.

Specific systems and devices have been described above and shown in the drawings. The invention also includes, in one embodiment, a method for measuring and communicating parameters of a brain, tissue or other organs. Referring to FIG. 21, the method includes the steps of providing a sensor 16 to sense the parameter of interest 106, implanting the sensor 16 in, on or near a target in the brain, tissue or other organ where the parameter of interest may be sensed 108, providing a reaction device where the parameter may be displayed, processed or cause action to be taken 110, sensing the parameter or interest 112, communicating the sensed parameter to the reaction device and displaying or processing the parameter or causing action to be taken in response to the parameter 114.

Figure 22:
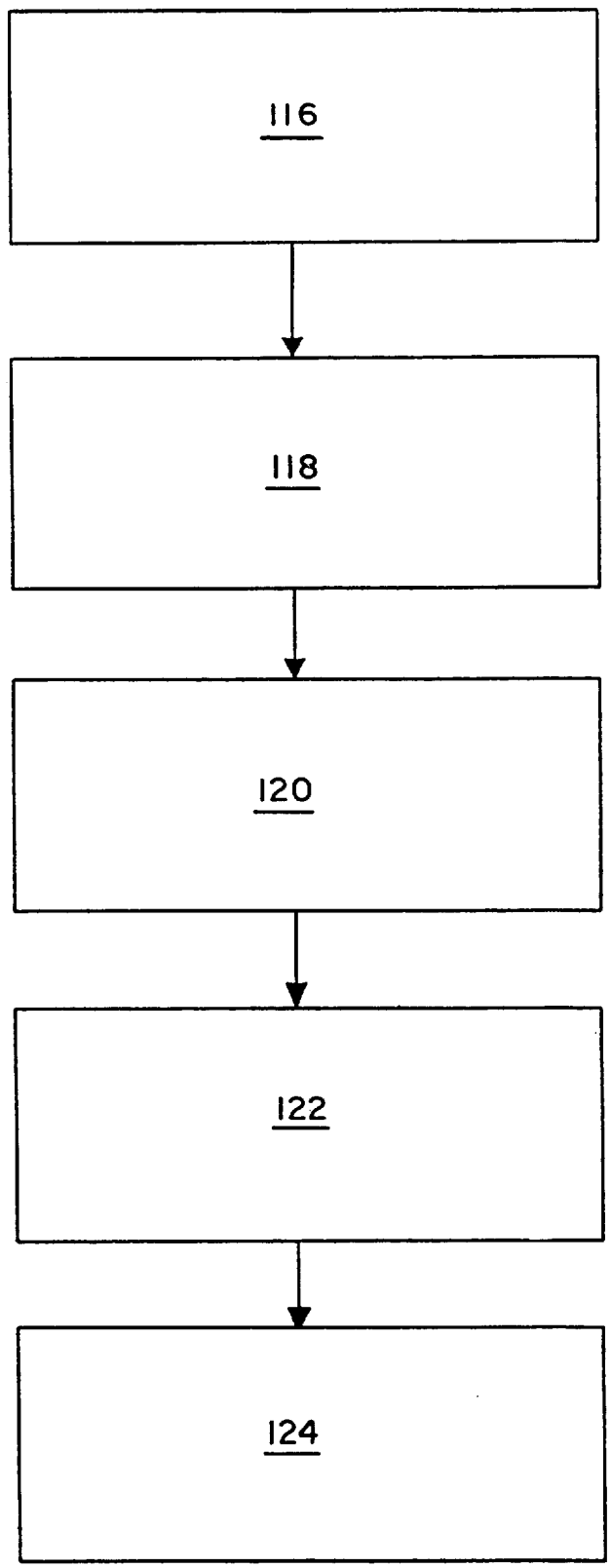
FIG. 22 is a flow chart showing another embodiment of the method of the invention.

A specific embodiment of the method of invention described above is shown in FIG. 22. In this embodiment, a method of controlling a CSF shunt drainage system is disclosed. This method comprises the steps of providing a probe having a sensor to sense a parameter of interest 116; providing a CSF shunt drainage system including a control device 104 to affect the flow of CSF fluid from a patient's ventricle to the CSF shunt drainage system 118; implanting the probe so that the sensor is located in the patient's ventricle 120; sensing the patient's CSF fluid pressure 122; and activating the control device 104 in response to the sensed parameter 124.

Figure 23:
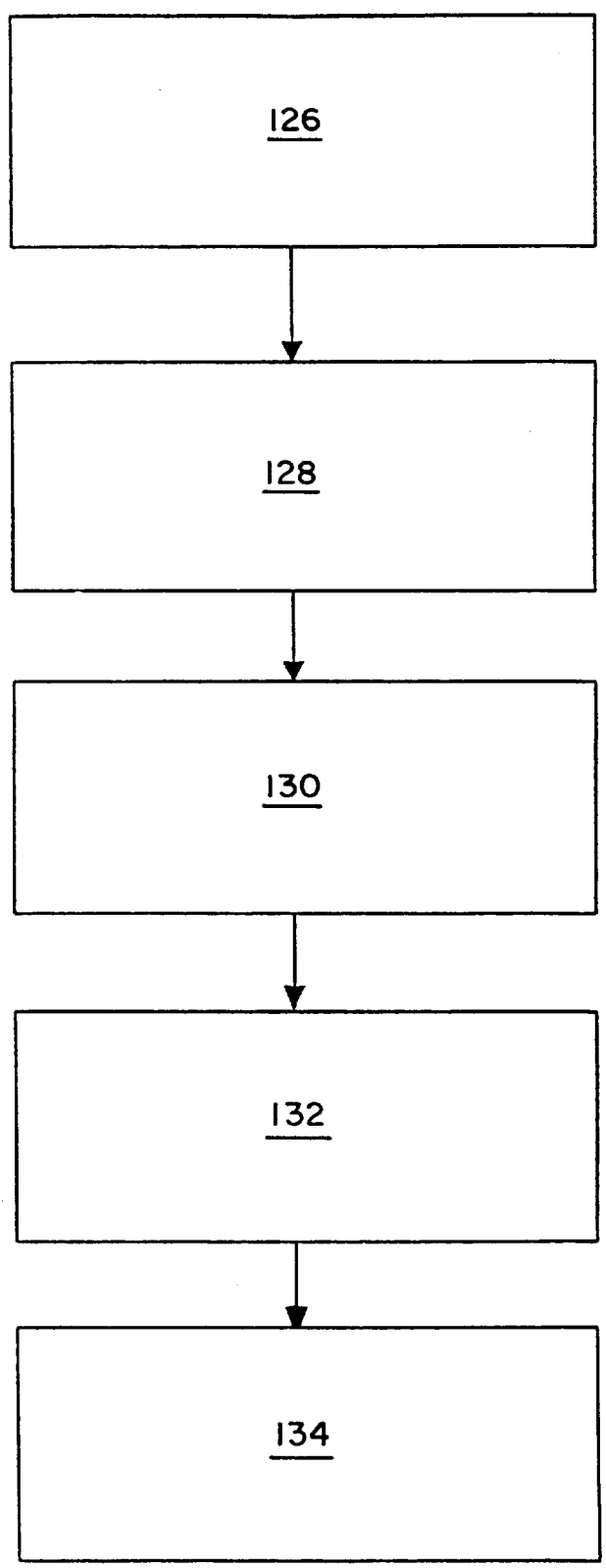
FIG. 23 is a flow chart showing another embodiment of the method of the invention.

In a further embodiment of the method of the invention, as shown in FIG. 23, a method of controlling a medical device in response to a sensed parameter is shown. This method comprises the steps of: providing a probe having a sensor to sense a parameter of interest 126; providing a medical device having a control device 104 that acts in response to the sensed parameter of interest to control the operation of the medical device 128; implanting the probe so that the sensor is located at a desired location in a patient 130; sensing the parameter of interest 132; and activating the control device 104 in response to the sensed parameter 134.

The step of providing a sensor 16 to sense the parameter of interest 106 or of providing a probe having a sensor to sense a parameter of interest 116, 126 includes providing a sensor 16 as described above and shown in the drawings. However, it is clear that while sensor 16 has primarily been described herein as a sensor to sense pressure or temperature, sensor 16 may also be a sensor that senses partial oxygen pressure ($PO_2$), mixed venous oxygen saturation ($SVO_2$), blood glucose and pH, to name but a few possibilities that will occur to those skilled in the art. Further, sensor 16 may sense more than one parameter either sequentially or simultaneously. Further, although sensor 16 has been described primarily as being part of a probe 12, in one embodiment, sensor 16 is not required to be part of a probe 12.

The step of implanting the sensor 16 in or near a target in the brain, tissue or other organ where the parameter of interest may be sensed 108 or of implanting the probe so that the sensor is located at a desired location in a patient 120, 130 includes cutting through the skin, and tissue or bone if necessary, placing the sensor 16 at the desired location in the brain, tissue or other organ, anchoring the sensor if necessary and surgically closing the skin so that the probe 12 is entirely contained under the patient's skin.

The step of providing a reaction device where the parameter may be displayed, processed or cause action to be taken 110 includes the steps, as described above and shown in the drawings, of alternately either providing an external device 14 or providing a microprocessor 102 on the probe 12 itself. The step of activating the control device 104 in response to the sensed parameter 124, 134 includes the steps of activating the control device 104 through an external device 14 or a microprocessor 104. In either case, the external device 14 or microprocessor 102 processes the parameter or causes action to be taken in response to the parameter and, in the case of the external device 14, may cause the parameter data to be displayed. Further, although the invention has primarily been described as having a microprocessor 104 on the probe 12 itself, microprocessor 104 may be on the external device 14, on the medical device to be activated or located separately from either an external device 14 (if one is present), probe 12 or separate medical device.

The step of displaying or processing the parameter or causing action to be taken in response to the parameter 112 includes displaying or processing the parameter or causing action to be taken in response to the parameter as described above.

The description contained herein is intended to be illustrative of the invention and not an exhaustive description. Many variations, combinations and alternatives to the disclosed embodiments will occur to one of ordinary skill in this art. Further, where specific values have been given, these values are intended to be illustrative of the invention and are not intended to be limiting. All these alternatives, combinations and variations are intended to be included within the scope of the attached claims. Those familiar with the art may recognize other equivalents to the specific embodiments described herein which equivalents are also intended to be encompassed by the claims attached hereto.

What is claimed is:

1. A device for measuring and communicating parameters of a brain, tissue or other organ comprising:
    an implanted probe having a distal end and a proximal end and a sensor located at the distal end of the probe to sense a parameter of the brain, tissue or other organ;
    an external device where the parameter may be displayed, processed or cause action to be taken; and
    a communication system to communicate the sensed parameter from the sensor to the external device;
    wherein the communication system includes a display system that communicates the sensed parameter information to a user.

2. The device of claim 1, wherein the display system includes a display screen that displays the sensed parameter information to the user.

3. The device of claim 1 wherein the communication system is connected to an external computer.

4. The device of claim 1 wherein the communication system includes an alarm that activates to alert the user when the sensed parameter is outside of a pre-determined range.

5. A device for measuring and communicating parameters of a brain, tissue or other organs comprising:
    an implanted probe having a distal end and a proximal end and a sensor located at the distal end of the probe to sense a parameter of the brain, tissue or other organs;
    an external device where the parameter may be displayed, processed or cause action to be taken;
    a communication system to communicate the sensed parameter from the sensor to the external device wirelessly.

6. The device of claim 5 wherein the sensor is a pressure sensor.

7. The device of claim 5 wherein the sensor is a temperature sensor.

8. The device of claim 5 wherein the sensor is chosen from a group consisting of a partial oxygen pressure ($PO_2$) sensor, mixed venous oxygen saturation ($SVO_2$) sensor, blood glucose sensor and pH sensor.

9. The device of claim 5 wherein the sensor is separated from the probe.

10. The device of claim 9 wherein the sensor is electronically connected to the probe through a body bus.

11. The device of claim 5 wherein the probe includes a microprocessor.

12. The device of claim 5 wherein the probe has a long-term energy source for powering itself and the sensor.

13. The device of claim 12 wherein the long-term energy source is rechargeable.

14. The device of claim 12 wherein the long-term energy source is a battery.

15. The device of claim 12 wherein the long-term energy source is a capacitor.

16. The device of claim 5 wherein the probe has a storage system that stores sensed parameter information.

17. The device of claim 16 wherein calibration coefficients, unique to each sensor, are stored in the storage device for the purpose of post-measurement processing to achieve an accurate report of the physiological parameters measured by the sensor.

18. The device of claim 5 further comprising a passive power system that provides power to the probe to allow parameter information to be sensed by the sensor and to allow the sensed parameter information to be communicated to the external device.

19. The device of claim 5 further comprising a cerebrospinal fluid (CSF) shunt or drainage system having a catheter placed in the ventricles of the brain, a shunt used as a conduit to transport CSF from one location in the body to another and a pump located between the catheter and the shunt wherein the pump operates in response to the sensed parameter of interest by the sensor.

20. The device of claim 5 further comprising a cerebrospinal fluid (CSF) shunt or drainage system having a catheter placed in the ventricles of the brain, a shunt used as a conduit to transport CSF from one location in the body to another and a valve located between the catheter and the shunt wherein the valve operates in response to the sensed parameter of interest by the sensor.

21. The device of claim 5 wherein calibration coefficients, unique to each sensor, are stored in the external device for the purpose of post-measurement processing to achieve an accurate report of the physiological parameters measured by the sensor.

22. The device of claim 5 wherein calibration coefficients, unique to each sensor, are stored in the probe for the purpose of post-measurement processing to achieve an accurate report of the physiological parameters measured by the sensor.

23. The device of claim 5 further comprising a probe head located at the proximal end of the probe.

24. The device of claim 23 wherein the probe head is roughly discoid in shape.

25. The device of claim 23 wherein the probe head includes an embedded probe coil.

26. The device of claim 25 wherein the probe coil is an inductive coil.

27. The device of claim 5 wherein the probe includes an electronics case containing the probe electronics.

28. The device of claim 27 wherein the probe includes a body between the sensor and the electronics case.

29. The device of claim 5 wherein the probe has a periphery and wherein the probe has screw threads placed around the periphery of the probe.

30. The device of claim 5 further comprising a buff-hole ring having an opening and wherein the probe is placed in the opening of the buff-hole ring.

31. A device for controlling a medical device in response to a sensed parameter of a brain comprising:
    a cerebrospinal fluid (CSF) shunt drainage system including a drainage catheter, adaptable to be placed in a patient's ventricle, a control device connected to the drainage catheter and a drainage bag, connected to the control device, wherein the control device affects the flow of CSF fluid from a patients' ventricle to the drainage bag;
    an implanted probe having a distal end and a proximal end and a sensor located at the distal end of the probe to sense the parameter of the brain, tissue or other organs, the probe including a processing system for processing sensed parameter information to produce a control signal that activates or inactivates the control device.

32. The device of claim 31 wherein the control device is a pump and wherein the pump, when activated, moves CSF fluid from the patient's ventricle to the drainage bag.

33. The device of claim 31 wherein the control device is a valve that, when activated, allows CSF fluid to move from a patient's ventricle to the drainage bag.

34. A device for controlling a medical device in response to a sensed parameter of a brain comprising:
- a cerebrospinal fluid (CSF) shunt drainage system including a first catheter, adaptable to be placed in a patient's ventricle, a control device connected to the first catheter and a second catheter, adaptable to be placed in a patient's atrium or peritoneal cavity and connected to the control device, wherein the control device affects the flow of CSF fluid from a patient's ventricle to the second catheter; and
- an implanted probe having a distal end and a proximal end and a sensor located at the distal end of the probe to sense the parameter of the brain, tissue or other organs, the probe including a processing system for processing sensed parameter information to produce a control signal that activates or inactivates the control device.

35. The device of claim 34 wherein the control device is a pump and wherein the pump, when activated, moves CSF fluid from the patient's ventricle to the patient's atrium or peritoneal cavity.

36. The device of claim 34 wherein the control device is a valve that, when activated, allows CSF fluid to move from a patient's ventricle to the patient's atrium or peritoneal cavity.

37. A device for controlling a medical device in response to a sensed parameter of a brain comprising:
- a cerebrospinal fluid (CSF) shunt drainage system including a drainage catheter, adaptable to be placed in a patient's ventricle, a control device connected to the drainage catheter, the control device including a processing system for processing sensed parameter information to produce a control signal that activates or inactivates the control device and a drainage bag, connected to the control device, wherein the control device affects the flow of CSF fluid from a patient's ventricle to the drainage bag;
- an implanted probe having a distal end and a proximal end and a sensor located at the distal end of the probe to sense the parameter of the brain, tissue or other organs.

38. The device of claim 37 wherein the control device is a pump and wherein the pump, when activated, moves CSF fluid from the patient's ventricle to the drainage bag.

39. The device of claim 37 wherein the control device is a valve that, when activated, allows CSF fluid to move from a patient's ventricle to the drainage bag.

40. A device for controlling a medical device in response to a sensed parameter of a brain comprising:
- a cerebrospinal fluid (CSF) shunt drainage system including a first catheter, adaptable to be placed in a patient's ventricle, a second catheter, adaptable to be placed in a patient's atrium or peritoneal cavity and a control device connected to the first catheter, the control device including a processing system for processing sensed parameter information to produce a control signal that activates or inactivates the control device and connected to the control device, wherein the control device affects the flow of CSF fluid from a patient's ventricle to the second catheter; and
- an implanted probe having a distal end and a proximal end and a sensor located at the distal end of the probe to sense the parameter of the brain, tissue or other organs.

41. The device of claim 40 wherein the control device is a pump and wherein the pump, when activated, moves CSF fluid from the patient's ventricle to the patient's atrium or peritoneal cavity.

42. The device of claim 40 wherein the control device is a valve that, when activated, allows CSF fluid to move from a patient's ventricle to the patient's atrium or peritoneal cavity.

43. A device for controlling a medical device in response to a sensed parameter of a brain comprising:
- a cerebrospinal fluid (CSF) shunt drainage system including a drainage catheter, adaptable to be placed in a patient's ventricle, a control device connected to the drainage catheter and a drainage bag, connected to the control device, wherein the control device affects the flow of CSF fluid from a patient's ventricle to the drainage bag;
- an implanted probe having a distal end and a proximal end and a sensor located at the distal end of the probe to sense the parameter of the brain, tissue or other organs;
- an external device including a processing system for processing sensed parameter information to produce a control signal that activates or inactivates the control device; and
- a communication system to communicate the sensed parameter from the sensor to the external device and from the external device to the control device.

44. The device of claim 43 wherein the control device is a pump and wherein the pump, when activated, moves CSF fluid from the patient's ventricle to the drainage bag.

45. The device of claim 43 wherein the control device is a valve that, when activated, allows CSF fluid to move from a patient's ventricle to the drainage bag.

46. A device for controlling a medical device in response to a sensed parameter of a brain comprising:
- a cerebrospinal fluid (CSF) shunt drainage system including a first catheter, adaptable to be placed in a patient's ventricle, a control device connected to the first catheter and a second catheter, adaptable to be placed in a patient's atrium or peritoneal cavity and connected to the control device, wherein the control device affects the flow of CSF fluid from a patient's ventricle to the second catheter;
- an implanted probe having a distal end and a proximal end and a sensor located at the distal end of the probe to sense the parameter of the brain, tissue or other organs;
- an external device including a processing system for processing sensed parameter information to produce a control signal that activates or inactivates the control device; and
- a communication system to communicate the sensed parameter form the sensor to the external device and from the external device to the control device.

47. The device of claim 46 wherein the control device is a pump and wherein the pump, when activated, moves CSF fluid from the patient's ventricle to the patient's atrium or peritoneal cavity.

48. The device of claim 46 wherein the control device is a valve that, when activated, allows CSF fluid to move from a patient's ventricle to the patient's atrium or peritoneal cavity.

49. A method of measuring a parameter of the brain, comprising the steps of:
- providing a probe having a sensor to sense the parameter of interest;
- providing an external device where the parameter may be displayed, processed or cause action to be taken;

providing a communication system to communicate the sensed parameter from the probe to the external device wirelessly;

exposing the skull of a patient;

drilling a hole in the skull;

implanting the probe so that the sensor is located within the skull;

closing the patient's skin so that the probe is entirely contained under the patient's skin;

bringing the external device near the probe so that the sensed parameter is transferred from the probe to the external device.

50. The method of claim 49 wherein the step of providing an external device includes the step of providing a system for providing power to the probe.

51. The method of claim 49 further comprising the step of storing sensed pressure or temperature information from the sensor on the probe to be transmitted to the external device at a later time.

52. The method of claim 49 wherein the step of providing a probe includes the step of providing a long term power source to provide power to the probe.

53. The method of claim 49 wherein the probe includes a microprocessor.

54. The method of claim 49 further comprising the step of controlling a CSF shunt drainage system in response to the sensed parameter.

55. A method of controlling a cerebrospinal fluid (CSF) shunt drainage system comprising the steps of:

providing a probe having a distal end and a proximal end and a sensor located at the distal end of the probe to sense the patient's CSF fluid pressure;

providing a CSF shunt drainage system including a control device to affect the flow of CSF fluid from a patient's ventricle to the CSF shunt drainage system;

implanting the probe so that the sensor is located in the patient's ventricle;

sensing the patient's CSF fluid pressure;

activating the control device in response to the sensed parameter.

56. The method of claim 55 wherein the step of providing a CSF shunt drainage system includes the step of providing a drainage catheter, adaptable to be placed in a patient's ventricle, coupled to the control device and a drainage bag also coupled to the control device.

57. The method of claim 55 wherein the step of providing a CSF shunt drainage system includes the step of providing a first catheter, adaptable to be placed in a patient's ventricle, coupled to the control device and a second catheter adaptable to be placed in a patient's atrium or peritoneal cavity.

58. The method of claim 55 wherein the step of providing a CSF shunt drainage system includes the steps of providing a first catheter, adaptable to be placed in a patient's ventricle, and providing a drainage bag and wherein the control device is a pump coupled to the first catheter and the drainage bag, which pump, when activated, moves CSF fluid from a patient's ventricle to the drainage bag.

59. The method of claim 55 wherein the step of providing a CSF shunt drainage system includes the steps of providing a first catheter, adaptable to be placed in a patient's ventricle, and providing a second catheter adaptable to be placed in a patient's ventricle, and providing a second catheter adaptable to be placed in a patient's atrium or peritoneal cavity and wherein the control device is a pump coupled to the first and second catheters, which pump, when activated, moves CSF fluid from a patient's ventricle to the patient's atrium or peritoneal cavity.

60. The method of claim 55 wherein the step of providing a CSF shunt drainage system includes the steps of providing a first catheter, adaptable to be placed in a patient's ventricle, and providing a drainage bag and wherein the control device is a valve coupled to the first catheter and the drainage bag, which valve, when activated, allows CSF fluid to move from a patient's ventricle to the drainage bag.

61. The method of claim 55 wherein the step of providing a CSF shunt drainage system includes the steps of providing a firs catheter, adaptable to be placed in a patient's ventricle, and providing a second catheter adaptable to be placed in a patient's atrium or peritoneal cavity and wherein the control device is a valve coupled to the first and second catheters, which valve, when activated, allows CSF fluid to move from a patient's ventricle to the patient's atrium or peritoneal cavity.

62. The method of claim 55 wherein the control device is a pump.

63. The method of claim 55 wherein the control device is a valve.

64. The method of claim 55 wherein the control device is connected to a microprocessor so that the microprocessor controls the control device.

65. The method of claim 55 wherein the step of activating the control device in response to the sensed parameter includes the step of determining that the CSF pressure exceeds a predetermined level and thereafter activating the control device.

66. The method of claim 65 wherein the step of activating the control device in response to the sensed parameter includes the step of determining that the CSF pressure has fallen to an acceptable level and thereafter de-activating the control device.

67. The method of claim 55 wherein the step of implanting the probe so that the sensor is located at a desired location in a patient includes the step of placing the sensor in or in contact with the parenchyma or ventricles of the brain where pressure or temperature information may be sensed.

68. The method of claim 55 wherein the step of implanting the probe so that the sensor is located at a desired location in a patient includes the step of placing the sensor in contact with or in the spinal column, organs of the body, tumors or growths, body tissue, joints, cavities, sinuses or spaces between organs or tissue.

69. A method of wirelessly controlling a medical device in response to a sensed parameter comprising the steps of:

providing a probe having a distal end and a proximal end and a sensor located at the distal end of the probe to sense a parameter of interest;

providing a medical device having a control device that acts in response to the sensed parameter of interest to control the operation of the medical device;

implanting the probe so that the sensor is located at a desired location in a patient;

sensing the parameter of interest;

wirelessly activating the control device in response to the sensed parameter.

70. The method of claim 69 wherein the step of providing a medical device includes the step of providing a first catheter, adaptable to be placed in a patient's ventricle, coupled to the control device and a second catheter adaptable to be placed in a patient's atrium or peritoneal cavity.

71. The method of claim 69 wherein the step of providing a medical device includes the steps of providing a first catheter, adaptable to be placed in a patient's ventricle, and providing a drainage bag and wherein the control device is a pump coupled to the first catheter and the drainage bag, which pump, when activated, moves CSF fluid from a patient's ventricle to the drainage bag.

72. The method of claim 69 wherein the step of providing a medical device includes the steps of providing a first catheter, adaptable to be placed in a patient's ventricle, and providing a second catheter adaptable to be placed in a patient's atrium or peritoneal cavity and wherein the control device is a pump coupled to the first and second catheters, which pump, when activated, moves CSF fluid from a patient's ventricle to the patient's atrium or peritoneal cavity.

73. The method of claim 69 wherein the step of providing a medical device includes the steps of providing a first catheter, adaptable to be placed in a patient's ventricle, and providing a drainage bag and wherein the control device is a valve coupled to the first catheter and the drainage bag, which valve, when activated, allows CSF fluid to move from a patient's ventricle to the drainage bag.

74. The method of claim 69 wherein the step of providing a medical device includes the steps of providing a first catheter, adaptable to be placed in a patient's ventricle, and providing a second catheter adaptable to be placed in a patient's atrium or peritoneal cavity and wherein the control device is a valve coupled to the first and second catheters, which valve, when activated, allows CSF fluid to move from a patient's ventricle to the patient's atrium or peritoneal cavity.

75. The method of claim 74 wherein the control device is a pump.

76. The method of claim 74 wherein the control device is a valve.

77. The method of claim 74 wherein the control device is connected to a microprocessor so that the microprocessor controls the control device.

78. The method of claim 74 wherein the step of activating the control device in response to the sensed parameter includes the step of determining that the sensed parameter is outside predetermined limits and thereafter activating the control device.

79. The method of claim 74 wherein the step of activating the control device in response to the sensed parameter includes the steps in determining that the parameter of interest is within predetermined limits and thereafter deactivating the control device.

80. The method of claim 74 wherein the step of implanting the probe so that the sensor is located at a desired location in a patient includes the step of placing the sensor in or in contact with the parenchyma or ventricles of the brain where pressure or temperature information may be sensed.

81. The method of claim 74 wherein the step of implanting the probe so that the sensor is located at a desired location in a patient includes the step of placing the sensor in contact with or in the spinal column, organs of the body, tumors or growths, body tissue, joints, cavities, sinuses or spaces between organs or tissue.

\* \* \* \* \*